United States Patent
Evans et al.

(10) Patent No.: US 8,574,149 B2
(45) Date of Patent: *Nov. 5, 2013

(54) ADJUSTABLE TISSUE SUPPORT MEMBER

(75) Inventors: Doug Evans, Snellville, GA (US);
Henry Holsten, Covington, GA (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/524,408

(22) Filed: Jun. 15, 2012

(65) Prior Publication Data

US 2012/0253110 A1 Oct. 4, 2012

Related U.S. Application Data

(63) Continuation of application No. 12/269,749, filed on Nov. 12, 2008, now Pat. No. 8,206,280.

(60) Provisional application No. 61/102,147, filed on Oct. 2, 2008, provisional application No. 61/025,461, filed on Feb. 1, 2008, provisional application No. 61/020,231, filed on Jan. 10, 2008, provisional application No. 60/987,469, filed on Nov. 13, 2007, provisional application No. 61/015,741, filed on Dec. 21, 2007.

(51) Int. Cl.
*A61F 2/00* (2006.01)

(52) U.S. Cl.
USPC .............................. 600/37; 600/30; 606/151

(58) Field of Classification Search
USPC ......... 600/29–32, 37; 606/151, 157; 128/885, 128/897, 898
See application file for complete search history.

(56) References Cited

U.S. PATENT DOCUMENTS

| 107,956 | A | 10/1870 | Peoble |
|---|---|---|---|
| 1,393,107 | A | 10/1921 | Fuller |
| 1,450,101 | A | 3/1923 | Mathewson |
| 1,758,261 | A | 5/1930 | Leland |
| 1,924,348 | A | 8/1933 | Brown |

(Continued)

FOREIGN PATENT DOCUMENTS

| CA | 2592617 C | 1/2012 |
|---|---|---|
| DE | 3223153 C1 | 8/1983 |

(Continued)

OTHER PUBLICATIONS

PCT/US2008/083381 filed Nov. 13, 2008 International Search Report dated Dec. 29, 2008.

(Continued)

*Primary Examiner* — Charles A Marmor, II
*Assistant Examiner* — Carrie R Dorna
(74) *Attorney, Agent, or Firm* — Rutan & Tucker, LLP

(57) ABSTRACT

A tissue support system including an implantable tissue support member is described. The tissue support member includes a tissue support portion, a first arm having a first end joined to a first end of the tissue support portion, a second arm having a first end joined to a second end of the tissue support portion, the second arm defining a lumen, a first tissue anchor fixed to a second end of the first arm, a second tissue anchor slidably positioned over the second arm, and a locking member disposed in the lumen of the second arm between the second tissue anchor and a second end of the second arm.

20 Claims, 12 Drawing Sheets

(56) References Cited

U.S. PATENT DOCUMENTS

| | | |
|---|---|---|
| 2,042,403 A | 5/1936 | Hrivnak |
| 2,097,018 A | 10/1937 | Chamberlin |
| 2,137,710 A | 11/1938 | Anderson |
| 2,240,330 A | 4/1941 | Flagg et al. |
| 2,427,176 A | 9/1947 | Aldeen |
| 2,518,994 A | 8/1950 | Miller |
| 2,641,249 A | 6/1953 | Brockman |
| 2,666,338 A | 1/1954 | Sandberg |
| 2,738,790 A | 3/1956 | Todt et al. |
| 3,124,136 A | 3/1964 | Usher |
| 3,126,600 A | 3/1964 | De Marre |
| 3,182,662 A | 5/1965 | Shirodkar |
| 3,249,104 A | 5/1966 | Johnstein |
| 3,311,110 A | 3/1967 | Singerman et al. |
| 3,340,494 A | 9/1967 | Gutshall |
| 3,384,073 A | 5/1968 | Van Winkle, Jr. |
| 3,453,729 A | 7/1969 | Larson |
| 3,472,232 A | 10/1969 | Earl |
| 3,580,313 A | 5/1971 | McKnight |
| 3,714,843 A | 2/1973 | Bracey |
| 3,739,430 A | 6/1973 | Kohke |
| 3,763,860 A | 10/1973 | Clarke |
| 3,777,737 A | 12/1973 | Bucalo |
| 3,789,828 A | 2/1974 | Schulte |
| 3,858,783 A | 1/1975 | Kapitanov et al. |
| 3,913,179 A | 10/1975 | Rhee |
| 3,924,633 A | 12/1975 | Cook et al. |
| 3,976,351 A | 8/1976 | Hopfe |
| 3,995,619 A | 12/1976 | Glatzer |
| 4,019,499 A | 4/1977 | Fitzgerald |
| 4,037,603 A | 7/1977 | Wendorff |
| 4,063,356 A | 12/1977 | Hepworth et al. |
| 4,069,956 A | 1/1978 | Shearer, Sr. et al. |
| 4,089,112 A | 5/1978 | Richards |
| 4,128,100 A | 12/1978 | Wendorff |
| 4,172,458 A | 10/1979 | Pereyra |
| 4,204,541 A | 5/1980 | Kapitanov |
| 4,232,445 A | 11/1980 | Ito et al. |
| 4,233,734 A | 11/1980 | Bies |
| 4,235,238 A | 11/1980 | Ogiu et al. |
| 4,246,660 A | 1/1981 | Wevers |
| 4,255,881 A | 3/1981 | Fralish |
| 4,258,716 A | 3/1981 | Sutherland et al. |
| 4,265,231 A | 5/1981 | Scheller, Jr. et al. |
| 4,281,660 A | 8/1981 | Fujiwara |
| 4,322,885 A | 4/1982 | Osada et al. |
| 4,361,958 A | 12/1982 | Gilbert et al. |
| 4,409,866 A | 10/1983 | McBride |
| 4,441,497 A | 4/1984 | Paudler |
| 4,452,245 A | 6/1984 | Usher |
| 4,455,690 A | 6/1984 | Homsy |
| 4,467,802 A | 8/1984 | Maslanka et al. |
| 4,509,516 A | 4/1985 | Richmond |
| 4,524,771 A | 6/1985 | McGregor et al. |
| 4,632,100 A | 12/1986 | Somers et al. |
| 4,655,221 A | 4/1987 | Devereux |
| 4,679,453 A | 7/1987 | Morita et al. |
| 4,712,458 A | 12/1987 | Mally |
| 4,718,419 A | 1/1988 | Okada et al. |
| 4,741,335 A | 5/1988 | Okada et al. |
| 4,773,416 A | 9/1988 | Hourahane |
| 4,775,380 A | 10/1988 | Seedhom et al. |
| 4,784,139 A | 11/1988 | Demos |
| 4,799,484 A | 1/1989 | Smith et al. |
| 4,857,041 A | 8/1989 | Annis et al. |
| 4,865,031 A | 9/1989 | O'Keeffe |
| 4,911,164 A | 3/1990 | Roth |
| 4,920,986 A | 5/1990 | Biswas |
| 4,938,760 A | 7/1990 | Burton et al. |
| 4,946,467 A | 8/1990 | Ohi et al. |
| 5,013,292 A | 5/1991 | Lemay et al. |
| 5,013,316 A | 5/1991 | Goble et al. |
| 5,026,371 A | 6/1991 | Rydell et al. |
| 5,027,674 A | 7/1991 | Nolte et al. |
| 5,029,489 A | 7/1991 | Burmeister et al. |
| 5,053,043 A | 10/1991 | Gottesman et al. |
| 5,084,054 A | 1/1992 | Bencini et al. |
| 5,085,661 A | 2/1992 | Moss |
| 5,112,344 A | 5/1992 | Petros |
| 5,122,155 A | 6/1992 | Eberbach |
| 5,123,428 A | 6/1992 | Schwarz |
| 5,123,910 A | 6/1992 | McIntosh |
| 5,149,329 A | 9/1992 | Richardson |
| 5,152,749 A | 10/1992 | Giesy et al. |
| 5,152,778 A | 10/1992 | Bales, Jr. et al. |
| 5,163,942 A | 11/1992 | Rydell |
| 5,171,233 A | 12/1992 | Amplatz et al. |
| 5,171,314 A | 12/1992 | Dulebohn |
| 5,188,636 A | 2/1993 | Fedotov |
| 5,201,741 A | 4/1993 | Dulebohn |
| 5,207,694 A | 5/1993 | Broome |
| 5,209,756 A | 5/1993 | Seedhom et al. |
| 5,234,436 A | 8/1993 | Eaton et al. |
| 5,246,452 A | 9/1993 | Sinnott |
| 5,250,033 A | 10/1993 | Evans et al. |
| 5,256,133 A | 10/1993 | Spitz |
| 5,269,063 A | 12/1993 | Okada et al. |
| 5,281,237 A | 1/1994 | Gimpelson |
| 5,304,187 A | 4/1994 | Green et al. |
| 5,311,858 A | 5/1994 | Adair |
| 5,328,077 A | 7/1994 | Lou |
| 5,333,624 A | 8/1994 | Tovey |
| 5,334,185 A | 8/1994 | Giesy et al. |
| 5,336,239 A | 8/1994 | Gimpelson |
| 5,337,736 A | 8/1994 | Reddy |
| 5,342,371 A | 8/1994 | Welter et al. |
| 5,356,432 A | 10/1994 | Rutkow et al. |
| 5,362,294 A | 11/1994 | Seitzinger |
| 5,368,595 A | 11/1994 | Lewis |
| 5,368,602 A | 11/1994 | de la Torre |
| 5,380,334 A | 1/1995 | Torrie et al. |
| 5,383,904 A | 1/1995 | Totakura et al. |
| 5,386,836 A | 2/1995 | Biswas |
| 5,397,332 A | 3/1995 | Kammerer et al. |
| 5,397,353 A | 3/1995 | Oliver et al. |
| 5,403,328 A | 4/1995 | Shallman |
| 5,413,598 A | 5/1995 | Moreland |
| 5,439,467 A | 8/1995 | Benderev et al. |
| 5,447,512 A | 9/1995 | Wilson et al. |
| 5,456,721 A | 10/1995 | Legrand |
| 5,473,796 A | 12/1995 | Fusillo |
| 5,474,543 A | 12/1995 | McKay |
| 5,486,183 A | 1/1996 | Middleman et al. |
| 5,497,553 A | 3/1996 | Chong et al. |
| 5,499,991 A | 3/1996 | Garman et al. |
| 5,500,000 A | 3/1996 | Feagin et al. |
| 5,501,692 A | 3/1996 | Riza |
| 5,502,896 A | 4/1996 | Chen et al. |
| 5,509,900 A | 4/1996 | Kirkman |
| 5,520,700 A | 5/1996 | Beyar et al. |
| 5,520,703 A | 5/1996 | Essig et al. |
| 5,522,833 A | 6/1996 | Stephens et al. |
| 5,542,948 A | 8/1996 | Weaver et al. |
| 5,544,664 A | 8/1996 | Benderev et al. |
| 5,549,619 A | 8/1996 | Peters et al. |
| 5,549,676 A | 8/1996 | Johnson |
| 5,562,678 A | 10/1996 | Booker |
| 5,562,685 A | 10/1996 | Mollenauer et al. |
| 5,562,688 A | 10/1996 | Riza |
| 5,562,689 A | 10/1996 | Green et al. |
| 5,569,269 A | 10/1996 | Hart et al. |
| 5,571,139 A | 11/1996 | Jenkins, Jr. |
| 5,573,530 A | 11/1996 | Fleury et al. |
| 5,591,163 A | 1/1997 | Thompson |
| 5,601,558 A | 2/1997 | Torrie et al. |
| 5,611,515 A | 3/1997 | Benderev et al. |
| 5,628,756 A | 5/1997 | Barker, Jr. et al. |
| 5,633,286 A | 5/1997 | Chen |
| 5,640,886 A | 6/1997 | Lai et al. |
| 5,643,320 A | 7/1997 | Lower et al. |
| 5,647,836 A | 7/1997 | Blake, III et al. |
| 5,655,270 A | 8/1997 | Boisvert |
| 5,662,683 A | 9/1997 | Kay |
| 5,667,513 A | 9/1997 | Torrie et al. |

(56) References Cited

U.S. PATENT DOCUMENTS

| | | |
|---|---|---|
| 5,669,935 A | 9/1997 | Rosenman et al. |
| 5,683,349 A | 11/1997 | Makower et al. |
| 5,689,860 A | 11/1997 | Matoba et al. |
| 5,693,072 A | 12/1997 | McIntosh |
| 5,702,397 A | 12/1997 | Goble et al. |
| 5,755,728 A | 5/1998 | Maki |
| 5,774,994 A | 7/1998 | Stein et al. |
| 5,792,142 A | 8/1998 | Galitzer |
| 5,807,403 A | 9/1998 | Beyar et al. |
| 5,810,882 A | 9/1998 | Bolduc et al. |
| 5,817,104 A | 10/1998 | Bilitz et al. |
| 5,817,128 A | 10/1998 | Storz et al. |
| 5,830,220 A | 11/1998 | Wan et al. |
| 5,836,053 A | 11/1998 | Davignon et al. |
| 5,836,314 A | 11/1998 | Benderev et al. |
| 5,836,315 A | 11/1998 | Benderev et al. |
| 5,840,011 A | 11/1998 | Landgrebe et al. |
| 5,842,478 A | 12/1998 | Benderev et al. |
| 5,846,248 A | 12/1998 | Chu et al. |
| 5,860,425 A | 1/1999 | Benderev et al. |
| 5,862,596 A | 1/1999 | Chung et al. |
| 5,864,952 A | 2/1999 | Chung et al. |
| 5,899,909 A | 5/1999 | Claren et al. |
| 5,904,692 A | 5/1999 | Steckel et al. |
| 5,904,696 A | 5/1999 | Rosenman |
| 5,910,148 A | 6/1999 | Reimels et al. |
| 5,919,232 A | 7/1999 | Chaffringeon et al. |
| 5,934,283 A | 8/1999 | Willem et al. |
| 5,935,122 A | 8/1999 | Fourkas et al. |
| 5,935,138 A | 8/1999 | McJames, II et al. |
| 5,944,732 A | 8/1999 | Raulerson et al. |
| 5,947,978 A | 9/1999 | Holsinger |
| 5,961,526 A | 10/1999 | Chu et al. |
| 5,968,008 A | 10/1999 | Grams |
| 5,971,967 A | 10/1999 | Willard |
| 5,972,000 A | 10/1999 | Beyar et al. |
| 5,987,751 A | 11/1999 | Chung et al. |
| 5,988,171 A | 11/1999 | Sohn et al. |
| 5,992,269 A | 11/1999 | Puig et al. |
| 5,993,459 A | 11/1999 | Larsen et al. |
| 5,997,554 A | 12/1999 | Thompson |
| 6,005,191 A | 12/1999 | Tzeng et al. |
| 6,006,433 A | 12/1999 | Baltazar |
| 6,010,447 A | 1/2000 | Kardjian |
| 6,030,393 A | 2/2000 | Corlew |
| 6,031,148 A | 2/2000 | Hayes et al. |
| 6,039,686 A | 3/2000 | Kovac |
| 6,042,534 A | 3/2000 | Gellman et al. |
| 6,042,536 A | 3/2000 | Tihon et al. |
| 6,048,351 A | 4/2000 | Gordon et al. |
| 6,048,354 A | 4/2000 | Lawrence |
| 6,050,937 A | 4/2000 | Benderev |
| 6,053,925 A | 4/2000 | Barnhart |
| 6,053,935 A | 4/2000 | Brenneman et al. |
| 6,056,688 A | 5/2000 | Benderev et al. |
| 6,059,796 A | 5/2000 | Bilitz et al. |
| 6,063,094 A | 5/2000 | Rosenberg et al. |
| 6,068,591 A | 5/2000 | Bruckner et al. |
| 6,068,648 A | 5/2000 | Cole et al. |
| 6,071,290 A | 6/2000 | Compton |
| 6,074,341 A | 6/2000 | Anderson et al. |
| 6,086,591 A | 7/2000 | Bojarski |
| 6,092,955 A | 7/2000 | Chartrain et al. |
| 6,096,041 A | 8/2000 | Gellman et al. |
| 6,096,060 A | 8/2000 | Fitts et al. |
| 6,099,538 A | 8/2000 | Moses et al. |
| 6,106,545 A | 8/2000 | Egan |
| 6,110,101 A | 8/2000 | Tihon et al. |
| 6,117,067 A | 9/2000 | Gil-Vernet |
| 6,117,162 A | 9/2000 | Schmieding et al. |
| 6,168,611 B1 | 1/2001 | Rizvi |
| 6,171,315 B1 | 1/2001 | Chu et al. |
| 6,197,036 B1 | 3/2001 | Tripp et al. |
| 6,200,330 B1 | 3/2001 | Benderev et al. |
| 6,210,416 B1 | 4/2001 | Chu et al. |
| 6,221,005 B1 | 4/2001 | Bruckner et al. |
| 6,221,060 B1 | 4/2001 | Willard |
| 6,226,873 B1 | 5/2001 | Okumura et al. |
| 6,235,026 B1 | 5/2001 | Smith |
| 6,273,852 B1 | 8/2001 | Lehe et al. |
| 6,290,702 B1 | 9/2001 | Fucci et al. |
| 6,293,961 B2 | 9/2001 | Schwartz et al. |
| 6,302,840 B1 | 10/2001 | Benderev |
| 6,306,079 B1 | 10/2001 | Trabucco |
| 6,306,159 B1 | 10/2001 | Schwartz et al. |
| 6,312,448 B1 | 11/2001 | Bonutti |
| 6,315,782 B1 | 11/2001 | Chu et al. |
| 6,319,271 B1 | 11/2001 | Schwartz et al. |
| 6,322,492 B1 | 11/2001 | Kovac |
| 6,328,686 B1 | 12/2001 | Kovac |
| 6,328,744 B1 | 12/2001 | Harari et al. |
| 6,328,758 B1 | 12/2001 | Tornier et al. |
| 6,334,446 B1 | 1/2002 | Beyar |
| 6,336,731 B1 | 1/2002 | Chien |
| 6,346,109 B1 | 2/2002 | Fucci et al. |
| 6,346,115 B1 | 2/2002 | Lawrence |
| 6,352,553 B1 | 3/2002 | van der Burg et al. |
| 6,355,065 B1 | 3/2002 | Gabbay |
| 6,358,197 B1 | 3/2002 | Silverman et al. |
| 6,367,353 B2 | 4/2002 | Brucart Puig et al. |
| 6,371,963 B1 | 4/2002 | Nishtala et al. |
| 6,375,661 B2 | 4/2002 | Chu et al. |
| 6,382,214 B1 | 5/2002 | Raz et al. |
| D458,679 S | 6/2002 | Thompson et al. |
| 6,406,423 B1 | 6/2002 | Scetbon et al. |
| 6,406,480 B1 | 6/2002 | Beyar et al. |
| 6,409,733 B1 | 6/2002 | Conlon et al. |
| 6,423,080 B1 | 7/2002 | Gellman et al. |
| 6,432,123 B2 | 8/2002 | Schwartz et al. |
| 6,440,154 B2 | 8/2002 | Gellman et al. |
| 6,475,139 B1 | 11/2002 | Miller |
| 6,478,727 B2 | 11/2002 | Scetbon et al. |
| 6,478,803 B1 | 11/2002 | Kapec et al. |
| 6,482,214 B1 | 11/2002 | Sidor, Jr. et al. |
| 6,491,703 B1 | 12/2002 | Ulmsten et al. |
| 6,491,714 B1 | 12/2002 | Bennett |
| 6,494,887 B1 | 12/2002 | Kaladelfos et al. |
| 6,494,906 B1 | 12/2002 | Owens |
| 6,502,578 B2 | 1/2003 | Raz et al. |
| 6,506,190 B1 | 1/2003 | Walshe |
| 6,511,499 B2 | 1/2003 | Schmieding et al. |
| 6,517,552 B1 | 2/2003 | Nord et al. |
| 6,530,943 B1 | 3/2003 | Hoepffner et al. |
| 6,537,198 B1 | 3/2003 | Vidlund et al. |
| 6,544,267 B1 | 4/2003 | Cole et al. |
| 6,553,674 B1 | 4/2003 | Budrow |
| 6,554,842 B2 | 4/2003 | Heuser et al. |
| 6,569,188 B2 | 5/2003 | Grafton et al. |
| 6,575,976 B2 | 6/2003 | Grafton |
| 6,575,984 B2 | 6/2003 | Beyar et al. |
| 6,575,998 B2 | 6/2003 | Beyar et al. |
| 6,582,443 B2 | 6/2003 | Cabak et al. |
| 6,591,838 B2 | 7/2003 | Durgin |
| 6,592,515 B2 | 7/2003 | Thierfelder et al. |
| 6,592,610 B2 | 7/2003 | Beyar et al. |
| 6,596,001 B2 | 7/2003 | Stormby et al. |
| 6,605,097 B1 | 8/2003 | Lehe et al. |
| 6,612,977 B2 | 9/2003 | Staskin et al. |
| 6,626,917 B1 | 9/2003 | Craig |
| 6,638,209 B2 | 10/2003 | Landgrebe et al. |
| 6,638,210 B2 | 10/2003 | Berger |
| 6,638,211 B2 | 10/2003 | Suslian et al. |
| 6,638,286 B1 | 10/2003 | Burbank et al. |
| 6,641,524 B2 | 11/2003 | Kovac |
| 6,641,525 B2 | 11/2003 | Rocheleau et al. |
| 6,652,450 B2 | 11/2003 | Neisz et al. |
| 6,652,537 B2 | 11/2003 | Mercereau et al. |
| 6,656,183 B2 | 12/2003 | Colleran et al. |
| 6,663,633 B1 | 12/2003 | Pierson, III |
| 6,663,645 B2 | 12/2003 | Nishtala et al. |
| 6,673,010 B2 | 1/2004 | Skiba et al. |
| 6,675,483 B2 | 1/2004 | Bond et al. |
| 6,676,668 B2 | 1/2004 | Mercereau et al. |
| 6,685,629 B2 | 2/2004 | Therin |

(56) References Cited

U.S. PATENT DOCUMENTS

| | | |
|---|---|---|
| 6,689,047 B2 | 2/2004 | Gellman |
| 6,691,711 B2 | 2/2004 | Raz et al. |
| 6,702,827 B1 | 3/2004 | Lund et al. |
| 6,708,410 B2 | 3/2004 | Okada et al. |
| 6,712,830 B2 | 3/2004 | Esplin |
| 6,730,097 B2 | 5/2004 | Dennis |
| 6,730,110 B1 | 5/2004 | Harari et al. |
| 6,736,854 B2 | 5/2004 | Vadurro et al. |
| 6,737,371 B1 | 5/2004 | Planck et al. |
| 6,746,472 B2 | 6/2004 | Frazier et al. |
| 6,752,814 B2 | 6/2004 | Gellman et al. |
| 6,755,781 B2 | 6/2004 | Gellman |
| 6,761,722 B2 | 7/2004 | Cole et al. |
| 6,789,326 B1 | 9/2004 | Huang et al. |
| 6,802,807 B2 | 10/2004 | Anderson et al. |
| 6,808,486 B1 | 10/2004 | O'Donnell |
| 6,808,487 B2 | 10/2004 | Migliari et al. |
| 6,835,193 B2 | 12/2004 | Epstein et al. |
| 6,843,792 B2 | 1/2005 | Nishtala et al. |
| 6,872,227 B2 | 3/2005 | Sump et al. |
| 6,878,134 B2 | 4/2005 | Rogers et al. |
| 6,881,184 B2 | 4/2005 | Zappala |
| 6,908,425 B2 | 6/2005 | Luscombe |
| 6,911,003 B2 | 6/2005 | Anderson et al. |
| 6,932,759 B2 | 8/2005 | Kammerer et al. |
| 6,936,052 B2 | 8/2005 | Gellman et al. |
| 6,953,428 B2 | 10/2005 | Gellman et al. |
| 6,960,160 B2 | 11/2005 | Browning et al. |
| 6,966,113 B2 | 11/2005 | Fossella |
| 6,971,390 B1 | 12/2005 | Vasek et al. |
| 6,971,986 B2 | 12/2005 | Staskin et al. |
| 6,986,781 B2 | 1/2006 | Smith |
| 6,987,995 B2 | 1/2006 | Drysen |
| 6,991,597 B2 | 1/2006 | Gellman et al. |
| 7,014,607 B2 | 3/2006 | Gellman |
| 7,025,063 B2 | 4/2006 | Snitkin et al. |
| 7,025,756 B2 | 4/2006 | Frazier et al. |
| 7,025,772 B2 | 4/2006 | Gellman et al. |
| 7,033,380 B2 | 4/2006 | Schwartz et al. |
| 7,037,255 B2 | 5/2006 | Inman et al. |
| 7,037,307 B2 | 5/2006 | Dennis |
| 7,037,324 B2 | 5/2006 | Martinek |
| 7,044,905 B2 | 5/2006 | Vidlund et al. |
| 7,048,682 B2 | 5/2006 | Neisz et al. |
| 7,052,495 B2 | 5/2006 | Smith |
| 7,056,333 B2 | 6/2006 | Walshe |
| 7,063,716 B2 | 6/2006 | Cunningham |
| 7,070,556 B2 | 7/2006 | Anderson et al. |
| 7,070,558 B2 | 7/2006 | Gellman et al. |
| 7,083,568 B2 | 8/2006 | Neisz et al. |
| 7,083,648 B2 | 8/2006 | Yu et al. |
| 7,087,065 B2 | 8/2006 | Ulmsten et al. |
| 7,094,199 B2 | 8/2006 | Petros et al. |
| 7,101,378 B2 | 9/2006 | Salameh et al. |
| 7,112,171 B2 | 9/2006 | Rocheleau et al. |
| 7,112,210 B2 | 9/2006 | Ulmsten et al. |
| 7,121,997 B2 | 10/2006 | Kammerer et al. |
| 7,131,943 B2 | 11/2006 | Kammerer |
| 7,131,944 B2 | 11/2006 | Jacquetin et al. |
| 7,163,506 B2 | 1/2007 | Grise |
| 7,198,597 B2 | 4/2007 | Siegel et al. |
| 7,204,801 B2 | 4/2007 | Grocela |
| 7,204,802 B2 | 4/2007 | De Leval et al. |
| RE39,626 E | 5/2007 | Tihon |
| D543,626 S | 5/2007 | Watschke et al. |
| 7,217,264 B2 | 5/2007 | Gobron et al. |
| 7,226,407 B2 | 6/2007 | Kammerer et al. |
| 7,226,408 B2 | 6/2007 | Harai et al. |
| 7,229,453 B2 | 6/2007 | Anderson et al. |
| 7,235,043 B2 | 6/2007 | Gellman et al. |
| 7,244,259 B2 | 7/2007 | Smith et al. |
| 7,261,723 B2 | 8/2007 | Smith et al. |
| 7,267,645 B2 | 9/2007 | Anderson et al. |
| 7,285,086 B2 | 10/2007 | Smith et al. |
| 7,288,063 B2 | 10/2007 | Petros et al. |
| 7,291,104 B2 | 11/2007 | Neisz et al. |
| 7,297,102 B2 | 11/2007 | Smith et al. |
| 7,303,525 B2 | 12/2007 | Watschke et al. |
| 7,326,213 B2 | 2/2008 | Benderev et al. |
| 7,338,432 B2 | 3/2008 | Valtchev |
| 7,347,812 B2 | 3/2008 | Mellier et al. |
| 7,347,813 B2 | 3/2008 | Claren et al. |
| 7,351,196 B2 | 4/2008 | Goldmann et al. |
| 7,351,197 B2 | 4/2008 | Montpetit et al. |
| 7,357,773 B2 | 4/2008 | Watschke |
| 7,364,541 B2 | 4/2008 | Chu et al. |
| 7,371,245 B2 | 5/2008 | Evans et al. |
| 7,387,634 B2 | 6/2008 | Benderev |
| 7,402,133 B2 | 7/2008 | Chu et al. |
| 7,404,819 B1 | 7/2008 | Darios et al. |
| 7,407,480 B2 | 8/2008 | Staskin et al. |
| 7,410,460 B2 | 8/2008 | Benderev |
| 7,413,540 B2 | 8/2008 | Gellman et al. |
| 7,422,557 B2 | 9/2008 | Arnal et al. |
| 7,500,945 B2 | 3/2009 | Cox et al. |
| 7,527,588 B2 | 5/2009 | Zaddem et al. |
| 7,588,598 B2 | 9/2009 | Delorme et al. |
| 7,611,454 B2 | 11/2009 | De Leval |
| 7,621,864 B2 | 11/2009 | Suslian et al. |
| 7,621,865 B2 | 11/2009 | Gellman et al. |
| 7,628,156 B2 | 12/2009 | Astani et al. |
| 7,658,743 B2 | 2/2010 | Ulmsten |
| 7,691,050 B2 | 4/2010 | Gellman et al. |
| 7,691,052 B2 | 4/2010 | Gellman et al. |
| 7,691,110 B2 | 4/2010 | Secrest et al. |
| 7,722,527 B2 | 5/2010 | Bouchier et al. |
| 7,771,345 B1 | 8/2010 | O'Donnell |
| 7,789,821 B2 | 9/2010 | Browning |
| 7,867,161 B2 | 1/2011 | Staskin et al. |
| 7,878,969 B2 | 2/2011 | Chu et al. |
| 7,896,848 B2 | 3/2011 | Charukhchian |
| 7,981,023 B2 | 7/2011 | Nowlin et al. |
| 7,988,615 B2 | 8/2011 | Anderson et al. |
| 8,007,430 B2 | 8/2011 | Browning |
| 8,033,983 B2 | 10/2011 | Chu et al. |
| 8,057,383 B2 | 11/2011 | Weiser et al. |
| 8,092,366 B2 | 1/2012 | Evans |
| 8,097,007 B2 | 1/2012 | Evans et al. |
| 8,123,671 B2 | 2/2012 | Evans |
| 8,206,280 B2 | 6/2012 | Evans et al. |
| 8,480,559 B2 | 7/2013 | Knapp et al. |
| 2001/0000533 A1 | 4/2001 | Kovac |
| 2001/0008549 A1 | 7/2001 | Hashimoto |
| 2001/0010008 A1 | 7/2001 | Gellman et al. |
| 2001/0049467 A1 | 12/2001 | Lehe et al. |
| 2001/0051807 A1 | 12/2001 | Grafton |
| 2001/0053916 A1 | 12/2001 | Rioux |
| 2002/0007222 A1 | 1/2002 | Desai |
| 2002/0022841 A1 | 2/2002 | Kovac |
| 2002/0028980 A1 | 3/2002 | Thierfelder et al. |
| 2002/0052653 A1 | 5/2002 | Durgin |
| 2002/0055748 A1 | 5/2002 | Gellman et al. |
| 2002/0058959 A1 | 5/2002 | Gellman |
| 2002/0068948 A1 | 6/2002 | Stormby et al. |
| 2002/0072694 A1 | 6/2002 | Snitkin et al. |
| 2002/0077526 A1 | 6/2002 | Kammerer et al. |
| 2002/0078964 A1 | 6/2002 | Kovac et al. |
| 2002/0082619 A1 | 6/2002 | Cabak et al. |
| 2002/0091373 A1 | 7/2002 | Berger |
| 2002/0091391 A1 | 7/2002 | Cole et al. |
| 2002/0095181 A1 | 7/2002 | Beyar |
| 2002/0099258 A1 | 7/2002 | Staskin et al. |
| 2002/0099259 A1* | 7/2002 | Anderson et al. ............... 600/29 |
| 2002/0099260 A1 | 7/2002 | Suslian et al. |
| 2002/0107430 A1 | 8/2002 | Neisz et al. |
| 2002/0107525 A1 | 8/2002 | Harari et al. |
| 2002/0115906 A1 | 8/2002 | Miller |
| 2002/0128670 A1 | 9/2002 | Ulmsten et al. |
| 2002/0138025 A1 | 9/2002 | Gellman et al. |
| 2002/0147382 A1 | 10/2002 | Neisz et al. |
| 2002/0151762 A1 | 10/2002 | Rocheleau et al. |
| 2002/0151909 A1 | 10/2002 | Gellman et al. |
| 2002/0151910 A1 | 10/2002 | Gellman et al. |
| 2002/0156487 A1 | 10/2002 | Gellman et al. |

(56) References Cited

U.S. PATENT DOCUMENTS

| | | |
|---|---|---|
| 2002/0156488 A1 | 10/2002 | Gellman et al. |
| 2002/0156489 A1 | 10/2002 | Gellman et al. |
| 2002/0165566 A1 | 11/2002 | Ulmsten |
| 2002/0188169 A1 | 12/2002 | Kammerer et al. |
| 2002/0188301 A1 | 12/2002 | Dallara et al. |
| 2003/0004395 A1 | 1/2003 | Therin |
| 2003/0009181 A1 | 1/2003 | Gellman et al. |
| 2003/0023136 A1 | 1/2003 | Raz et al. |
| 2003/0023137 A1 | 1/2003 | Gellman |
| 2003/0023138 A1 | 1/2003 | Luscombe |
| 2003/0036676 A1 | 2/2003 | Scetbon |
| 2003/0036770 A1 | 2/2003 | Markman |
| 2003/0045774 A1 | 3/2003 | Staskin et al. |
| 2003/0045892 A1 | 3/2003 | Kaladelfos |
| 2003/0050530 A1 | 3/2003 | Neisz et al. |
| 2003/0065246 A1 | 4/2003 | Inman et al. |
| 2003/0065402 A1 | 4/2003 | Anderson et al. |
| 2003/0078604 A1 | 4/2003 | Walshe |
| 2003/0088250 A1 | 5/2003 | Colleran et al. |
| 2003/0130670 A1 | 7/2003 | Anderson et al. |
| 2003/0135239 A1 | 7/2003 | Gabriel et al. |
| 2003/0149440 A1 | 8/2003 | Kammerer et al. |
| 2003/0171644 A1 | 9/2003 | Anderson et al. |
| 2003/0176762 A1 | 9/2003 | Kammerer |
| 2003/0176875 A1 | 9/2003 | Anderson et al. |
| 2003/0191360 A1 | 10/2003 | Browning |
| 2003/0199732 A1 | 10/2003 | Suslian et al. |
| 2003/0212305 A1 | 11/2003 | Anderson et al. |
| 2003/0216693 A1 | 11/2003 | Mickley |
| 2003/0220538 A1 | 11/2003 | Jacquetin |
| 2003/0225424 A1 | 12/2003 | Benderev |
| 2003/0229350 A1 | 12/2003 | Kay |
| 2004/0006353 A1 | 1/2004 | Bosley et al. |
| 2004/0015048 A1 | 1/2004 | Neisz et al. |
| 2004/0015057 A1 | 1/2004 | Rocheleau et al. |
| 2004/0039246 A1 | 2/2004 | Gellman et al. |
| 2004/0039453 A1 | 2/2004 | Anderson et al. |
| 2004/0040159 A1 | 3/2004 | Fossella |
| 2004/0044364 A1 | 3/2004 | DeVries et al. |
| 2004/0059336 A1 | 3/2004 | Lombardo et al. |
| 2004/0068159 A1 | 4/2004 | Neisz et al. |
| 2004/0073219 A1 | 4/2004 | Skiba et al. |
| 2004/0073234 A1 | 4/2004 | Chu et al. |
| 2004/0087970 A1 | 5/2004 | Chu et al. |
| 2004/0087980 A1 | 5/2004 | Ford et al. |
| 2004/0097974 A1 | 5/2004 | De Leval |
| 2004/0097975 A1 | 5/2004 | Rose |
| 2004/0106845 A1 | 6/2004 | Anderson et al. |
| 2004/0106847 A1 | 6/2004 | Benderev |
| 2004/0106925 A1 | 6/2004 | Culbert |
| 2004/0111895 A1 | 6/2004 | Huang |
| 2004/0116774 A1 | 6/2004 | Migliari |
| 2004/0116944 A1 | 6/2004 | Chu et al. |
| 2004/0122474 A1 | 6/2004 | Gellman et al. |
| 2004/0133217 A1 | 7/2004 | Watschke |
| 2004/0144395 A1 | 7/2004 | Evans et al. |
| 2004/0153008 A1 | 8/2004 | Sharf et al. |
| 2004/0153074 A1 | 8/2004 | Bojarski et al. |
| 2004/0153103 A1 | 8/2004 | Schwartz et al. |
| 2004/0172048 A1 | 9/2004 | Browning |
| 2004/0209538 A1 | 10/2004 | Klinge et al. |
| 2004/0220595 A1 | 11/2004 | Frazier et al. |
| 2004/0225181 A1 | 11/2004 | Chu et al. |
| 2004/0225301 A1 | 11/2004 | Roop et al. |
| 2004/0230206 A1 | 11/2004 | Gellman et al. |
| 2004/0230207 A1 | 11/2004 | Gellman et al. |
| 2004/0231678 A1 | 11/2004 | Fierro |
| 2004/0249240 A1 | 12/2004 | Goldmann et al. |
| 2004/0249396 A1 | 12/2004 | Lund et al. |
| 2004/0249473 A1 | 12/2004 | Delorme et al. |
| 2004/0254609 A1 | 12/2004 | Esplin |
| 2004/0267088 A1 | 12/2004 | Kammerer |
| 2005/0004576 A1 | 1/2005 | Benderev |
| 2005/0021086 A1 | 1/2005 | De Leval |
| 2005/0028380 A1 | 2/2005 | Fossella |
| 2005/0033365 A1 | 2/2005 | Courage |
| 2005/0038370 A1 | 2/2005 | Kuth et al. |
| 2005/0043580 A1 | 2/2005 | Watschke et al. |
| 2005/0065395 A1 | 3/2005 | Mellier |
| 2005/0070829 A1 | 3/2005 | Therin et al. |
| 2005/0075654 A1 | 4/2005 | Kelleher |
| 2005/0075660 A1 | 4/2005 | Chu et al. |
| 2005/0085831 A1 | 4/2005 | Rioux |
| 2005/0090706 A1 | 4/2005 | Gellman et al. |
| 2005/0090841 A1 | 4/2005 | Morrison |
| 2005/0101834 A1 | 5/2005 | Merade |
| 2005/0101973 A1 | 5/2005 | Smith et al. |
| 2005/0107660 A1 | 5/2005 | Valtchev |
| 2005/0113845 A1 | 5/2005 | Griego et al. |
| 2005/0131274 A1 | 6/2005 | Suslian et al. |
| 2005/0131391 A1 | 6/2005 | Chu |
| 2005/0131392 A1 | 6/2005 | Chu et al. |
| 2005/0131393 A1 | 6/2005 | Chu et al. |
| 2005/0131429 A1 | 6/2005 | Ho et al. |
| 2005/0143618 A1 | 6/2005 | Anderson et al. |
| 2005/0148813 A1 | 7/2005 | Claren et al. |
| 2005/0149122 A1 | 7/2005 | McDevitt et al. |
| 2005/0177022 A1 | 8/2005 | Chu et al. |
| 2005/0228413 A1 | 10/2005 | Binmoeller et al. |
| 2005/0234291 A1 | 10/2005 | Gingras |
| 2005/0240076 A1 | 10/2005 | Neisz et al. |
| 2005/0251083 A1 | 11/2005 | Carr-Brendel et al. |
| 2005/0251159 A1 | 11/2005 | Ewers et al. |
| 2005/0251177 A1 | 11/2005 | Saadat et al. |
| 2005/0251202 A1 | 11/2005 | Ewers et al. |
| 2005/0251210 A1 | 11/2005 | Westra et al. |
| 2005/0256366 A1 | 11/2005 | Chu |
| 2005/0256530 A1 | 11/2005 | Petros |
| 2005/0261545 A1 | 11/2005 | Gellman et al. |
| 2005/0273138 A1 | 12/2005 | To et al. |
| 2005/0277806 A1 | 12/2005 | Cristalli |
| 2005/0277807 A1 | 12/2005 | MacLean et al. |
| 2005/0277966 A1 | 12/2005 | Ewers et al. |
| 2005/0277981 A1 | 12/2005 | Maahs et al. |
| 2005/0283040 A1 | 12/2005 | Greenhalgh |
| 2005/0288689 A1 | 12/2005 | Kammerer et al. |
| 2006/0015001 A1 | 1/2006 | Staskin et al. |
| 2006/0015069 A1 | 1/2006 | Evans et al. |
| 2006/0025649 A1 | 2/2006 | Smith et al. |
| 2006/0041185 A1 | 2/2006 | Browning |
| 2006/0058574 A1 | 3/2006 | Priewe et al. |
| 2006/0058575 A1 | 3/2006 | Zaddem et al. |
| 2006/0058578 A1 | 3/2006 | Browning |
| 2006/0059693 A1 | 3/2006 | Fossella |
| 2006/0059695 A1 | 3/2006 | Levine et al. |
| 2006/0063968 A1 | 3/2006 | Anderson et al. |
| 2006/0089524 A1 | 4/2006 | Chu |
| 2006/0089525 A1 | 4/2006 | Mamo et al. |
| 2006/0100628 A1 | 5/2006 | Martinek |
| 2006/0106277 A1 | 5/2006 | Romero Maroto |
| 2006/0116719 A1 | 6/2006 | Martinek |
| 2006/0122457 A1 | 6/2006 | Kovac et al. |
| 2006/0130848 A1 | 6/2006 | Carey |
| 2006/0134159 A1 | 6/2006 | Nicita |
| 2006/0149123 A1 | 7/2006 | Vidlund et al. |
| 2006/0173237 A1 | 8/2006 | Jacquetin |
| 2006/0173468 A1 | 8/2006 | Simmon et al. |
| 2006/0173471 A1 | 8/2006 | Carr, Jr. et al. |
| 2006/0173864 A1 | 8/2006 | Dart et al. |
| 2006/0183966 A1 | 8/2006 | Neisz et al. |
| 2006/0184234 A1 | 8/2006 | Frazier et al. |
| 2006/0195007 A1 | 8/2006 | Anderson et al. |
| 2006/0195010 A1 | 8/2006 | Arnal et al. |
| 2006/0195011 A1 | 8/2006 | Arnal et al. |
| 2006/0195013 A1 | 8/2006 | Gellman et al. |
| 2006/0196137 A1 | 9/2006 | Brenzel et al. |
| 2006/0199994 A1 | 9/2006 | Inman et al. |
| 2006/0199996 A1 | 9/2006 | Caraballo et al. |
| 2006/0201519 A1 | 9/2006 | Frazier et al. |
| 2006/0205995 A1 | 9/2006 | Browning |
| 2006/0205998 A1 | 9/2006 | Li et al. |
| 2006/0207606 A1 | 9/2006 | Roue et al. |
| 2006/0217762 A1 | 9/2006 | Maahs et al. |
| 2006/0229493 A1 | 10/2006 | Weiser et al. |

(56) References Cited

U.S. PATENT DOCUMENTS

| | | |
|---|---|---|
| 2006/0229596 A1 | 10/2006 | Weiser et al. |
| 2006/0235262 A1 | 10/2006 | Arnal et al. |
| 2006/0235447 A1 | 10/2006 | Walshe |
| 2006/0247490 A1 | 11/2006 | Merade et al. |
| 2006/0252980 A1 | 11/2006 | Arnal et al. |
| 2006/0258897 A1 | 11/2006 | Petros et al. |
| 2006/0258898 A1 | 11/2006 | Montpetit et al. |
| 2006/0260618 A1 | 11/2006 | Hodroff et al. |
| 2006/0264698 A1 | 11/2006 | Kondonis et al. |
| 2006/0287571 A1 | 12/2006 | Gozzi et al. |
| 2007/0010830 A1 | 1/2007 | Gellman et al. |
| 2007/0015957 A1 | 1/2007 | Li |
| 2007/0021649 A1 | 1/2007 | Nowlin et al. |
| 2007/0021650 A1 | 1/2007 | Rocheleau et al. |
| 2007/0021686 A1 | 1/2007 | Gellman et al. |
| 2007/0032695 A1 | 2/2007 | Weiser |
| 2007/0038017 A1 | 2/2007 | Chu |
| 2007/0038018 A1 | 2/2007 | Chu |
| 2007/0043255 A1 | 2/2007 | O'Donnell |
| 2007/0043336 A1 | 2/2007 | Griffin et al. |
| 2007/0049790 A1 | 3/2007 | Wagner et al. |
| 2007/0049791 A1 | 3/2007 | Merade et al. |
| 2007/0055094 A1 | 3/2007 | Chen |
| 2007/0055095 A1 | 3/2007 | Chu et al. |
| 2007/0060788 A1 | 3/2007 | Gellman |
| 2007/0062541 A1 | 3/2007 | Zhou et al. |
| 2007/0068538 A1 | 3/2007 | Anderson et al. |
| 2007/0078295 A1 | 4/2007 | Landgrebe |
| 2007/0088390 A1 | 4/2007 | Paz et al. |
| 2007/0089750 A1 | 4/2007 | Astani et al. |
| 2007/0089751 A1 | 4/2007 | Astani et al. |
| 2007/0123746 A1 | 5/2007 | MacLean |
| 2007/0142698 A1 | 6/2007 | Bourne et al. |
| 2007/0156012 A1 | 7/2007 | Tracey et al. |
| 2007/0161849 A1 | 7/2007 | Goldberg |
| 2007/0203429 A1 | 8/2007 | Ziv |
| 2007/0225546 A1 | 9/2007 | Anderson et al. |
| 2007/0299299 A1 | 12/2007 | Rosenblatt |
| 2007/0299300 A1 | 12/2007 | Smith et al. |
| 2008/0004490 A1 | 1/2008 | Bosley et al. |
| 2008/0009665 A1 | 1/2008 | Merade et al. |
| 2008/0009667 A1 | 1/2008 | Longhini et al. |
| 2008/0009888 A1 | 1/2008 | Ewers et al. |
| 2008/0039678 A1 | 2/2008 | Montpetit et al. |
| 2008/0045782 A1 | 2/2008 | Jimenez |
| 2008/0082121 A1 | 4/2008 | Chu |
| 2008/0097329 A1 | 4/2008 | Hodroff et al. |
| 2008/0132753 A1 | 6/2008 | Goddard |
| 2008/0269547 A1 | 10/2008 | Hortenstine |
| 2008/0281148 A1 | 11/2008 | Evans et al. |
| 2008/0300607 A1 | 12/2008 | Meade et al. |
| 2009/0105743 A1 | 4/2009 | Chu |
| 2009/0137862 A1 | 5/2009 | Evans et al. |
| 2009/0149700 A1 | 6/2009 | Garcia et al. |
| 2009/0221868 A1 | 9/2009 | Evans |
| 2009/0306464 A1 | 12/2009 | Griguol |
| 2009/0318752 A1 | 12/2009 | Evans et al. |
| 2010/0010501 A2 | 1/2010 | Meade et al. |
| 2010/0030015 A1 | 2/2010 | Delorme et al. |
| 2010/0056856 A1 | 3/2010 | Suslian et al. |
| 2010/0197999 A1 | 8/2010 | Deegan et al. |
| 2010/0217069 A1 | 8/2010 | Meade et al. |
| 2010/0234679 A1 | 9/2010 | Evans |
| 2010/0234681 A1 | 9/2010 | Knapp et al. |
| 2010/0241105 A1 | 9/2010 | Meade et al. |
| 2011/0082328 A1 | 4/2011 | Gozzi et al. |
| 2011/0105833 A1 | 5/2011 | Gozzi et al. |
| 2011/0124954 A1 | 5/2011 | Ogdahl et al. |
| 2011/0282133 A1 | 11/2011 | Anderson et al. |
| 2012/0029488 A1 | 2/2012 | Chu |
| 2012/0108890 A1 | 5/2012 | Evans |
| 2012/0116154 A1 | 5/2012 | Evans et al. |

FOREIGN PATENT DOCUMENTS

| | | |
|---|---|---|
| DE | 4220283 A1 | 12/1993 |
| DE | 4334419 A1 | 4/1995 |
| DE | 19544162 C1 | 4/1997 |
| DE | 10138950 A1 | 2/2003 |
| DE | 102 11 360 A1 | 10/2003 |
| DE | 10245076 A1 | 4/2004 |
| EP | 0437481 A1 | 7/1991 |
| EP | 0537769 A1 | 4/1993 |
| EP | 0556313 | 8/1993 |
| EP | 0557964 A1 | 9/1993 |
| EP | 0598976 A2 | 6/1994 |
| EP | 0619984 A1 | 10/1994 |
| EP | 0648474 A1 | 4/1995 |
| EP | 0668056 A1 | 8/1995 |
| EP | 0692225 A2 | 1/1996 |
| EP | 0740925 | 11/1996 |
| EP | 0745351 | 12/1996 |
| EP | 0774240 A1 | 5/1997 |
| EP | 0778749 | 6/1997 |
| EP | 0854691 | 7/1998 |
| EP | 0913162 A1 | 5/1999 |
| EP | 0941712 A1 | 9/1999 |
| EP | 0983033 B1 | 3/2000 |
| EP | 1018980 B1 | 7/2000 |
| EP | 1093758 | 4/2001 |
| EP | 1151722 | 11/2001 |
| EP | 1159920 A2 | 12/2001 |
| EP | 1159921 | 12/2001 |
| EP | 1239793 B1 | 9/2002 |
| EP | 1239795 B1 | 9/2002 |
| EP | 1342450 A1 | 9/2003 |
| EP | 1342454 A1 | 9/2003 |
| EP | 1399082 B1 | 3/2004 |
| EP | 1417934 A2 | 5/2004 |
| EP | 1487377 A1 | 12/2004 |
| EP | 1534154 | 6/2005 |
| EP | 1549245 B1 | 7/2005 |
| EP | 1600118 A1 | 11/2005 |
| EP | 1609439 A1 | 12/2005 |
| EP | 1610714 A2 | 1/2006 |
| EP | 1688105 A2 | 8/2006 |
| EP | 1909672 A2 | 4/2008 |
| EP | 1545285 B1 | 11/2010 |
| EP | 1948073 A4 | 3/2011 |
| FR | 2712177 A1 | 5/1995 |
| FR | 2785521 | 5/2000 |
| FR | 0102120 | 1/2002 |
| FR | 2852817 A1 | 10/2004 |
| FR | 2859624 A1 | 3/2005 |
| FR | 2859901 A1 | 3/2005 |
| GB | 2382993 B | 6/2003 |
| JP | 03070567 A | 3/1991 |
| JP | 05161655 A | 6/1993 |
| JP | 11221221 A | 8/1999 |
| JP | 2002503510 A | 2/2002 |
| JP | 2002143290 A | 5/2002 |
| JP | 2003501144 A | 1/2003 |
| JP | 2003225240 A | 8/2003 |
| JP | 2005505313 A | 2/2005 |
| JP | 2005534422 A | 11/2005 |
| JP | 4452180 B2 | 4/2010 |
| SE | 503271 C2 | 4/1996 |
| WO | 9003766 | 4/1990 |
| WO | 9003766 A1 | 4/1990 |
| WO | 9208412 A1 | 5/1992 |
| WO | 9310731 A1 | 6/1993 |
| WO | 9315690 A2 | 8/1993 |
| WO | 9603091 A1 | 2/1996 |
| WO | 9606567 | 3/1996 |
| WO | 9606567 A1 | 3/1996 |
| WO | 9606597 A1 | 3/1996 |
| WO | 9607355 A1 | 3/1996 |
| WO | 9608587 A1 | 3/1996 |
| WO | 9640307 A1 | 12/1996 |
| WO | 9713465 | 4/1997 |
| WO | 9713465 A1 | 4/1997 |
| WO | 9716121 | 5/1997 |

(56) References Cited

FOREIGN PATENT DOCUMENTS

| | | |
|---|---|---|
| WO | 9743982 A1 | 11/1997 |
| WO | 9831301 A1 | 7/1998 |
| WO | 9835632 | 8/1998 |
| WO | 9835632 A1 | 8/1998 |
| WO | 9922873 A1 | 5/1999 |
| WO | 9934744 A1 | 7/1999 |
| WO | 9942041 A1 | 8/1999 |
| WO | 9959477 A1 | 11/1999 |
| WO | 0018325 | 4/2000 |
| WO | 0027304 | 5/2000 |
| WO | 0027304 A1 | 5/2000 |
| WO | 0040158 A2 | 7/2000 |
| WO | 0064370 A1 | 11/2000 |
| WO | 0066030 | 11/2000 |
| WO | 0074594 | 12/2000 |
| WO | 0074594 A1 | 12/2000 |
| WO | 0074613 | 12/2000 |
| WO | 0074613 A1 | 12/2000 |
| WO | 0074633 | 12/2000 |
| WO | 0106951 A1 | 2/2001 |
| WO | 0130246 | 5/2001 |
| WO | 0147438 A1 | 7/2001 |
| WO | 0152750 | 7/2001 |
| WO | 0180774 A1 | 11/2001 |
| WO | 0193656 A2 | 12/2001 |
| WO | 0202031 | 1/2002 |
| WO | 0202031 A1 | 1/2002 |
| WO | 0219945 A2 | 3/2002 |
| WO | 0219946 | 3/2002 |
| WO | 0226108 | 4/2002 |
| WO | 0228312 | 4/2002 |
| WO | 0228312 A1 | 4/2002 |
| WO | 0228315 | 4/2002 |
| WO | 0232284 A2 | 4/2002 |
| WO | 0238079 A2 | 5/2002 |
| WO | 0239890 A2 | 5/2002 |
| WO | 0239914 | 5/2002 |
| WO | 02058562 | 8/2002 |
| WO | 02058562 A1 | 8/2002 |
| WO | 02058563 A1 | 8/2002 |
| WO | 02058564 | 8/2002 |
| WO | 02058565 | 8/2002 |
| WO | 02058565 A2 | 8/2002 |
| WO | 02062237 | 8/2002 |
| WO | 02065921 | 8/2002 |
| WO | 02065922 | 8/2002 |
| WO | 02065923 | 8/2002 |
| WO | 02065923 A1 | 8/2002 |
| WO | 02069781 A2 | 9/2002 |
| WO | 02071931 | 9/2002 |
| WO | 02071931 A1 | 9/2002 |
| WO | 02078548 A1 | 10/2002 |
| WO | 02098322 | 12/2002 |
| WO | 02098322 A1 | 12/2002 |
| WO | 03002027 | 1/2003 |
| WO | 03002027 A1 | 1/2003 |
| WO | 03013369 | 2/2003 |
| WO | 03028585 A2 | 4/2003 |
| WO | 03037215 A2 | 5/2003 |
| WO | 03053252 A1 | 7/2003 |
| WO | 03068107 | 8/2003 |
| WO | 03068107 A1 | 8/2003 |
| WO | 03073960 A1 | 9/2003 |
| WO | 03075792 | 9/2003 |
| WO | 03086205 A2 | 10/2003 |
| WO | 03092546 | 11/2003 |
| WO | 03096928 | 11/2003 |
| WO | 03096929 A1 | 11/2003 |
| WO | 03096930 | 11/2003 |
| WO | 03096930 A1 | 11/2003 |
| WO | 03101344 A1 | 12/2003 |
| WO | 2004004600 A1 | 1/2004 |
| WO | 2004008977 A1 | 1/2004 |
| WO | 2004012579 A2 | 2/2004 |
| WO | 2004012626 A1 | 2/2004 |
| WO | 2004016196 A2 | 2/2004 |
| WO | 2004017862 A2 | 3/2004 |
| WO | 2004019786 | 3/2004 |
| WO | 2004034912 A1 | 4/2004 |
| WO | 2004056273 A1 | 7/2004 |
| WO | 2004086983 A1 | 10/2004 |
| WO | 2004091442 A2 | 10/2004 |
| WO | 2004098461 A2 | 11/2004 |
| WO | 2005037132 A2 | 4/2005 |
| WO | 2005087153 A2 | 9/2005 |
| WO | 2005094741 A1 | 10/2005 |
| WO | 2005110273 A1 | 11/2005 |
| WO | 2005110274 A2 | 11/2005 |
| WO | 2005112842 A1 | 12/2005 |
| WO | 2005122954 A1 | 12/2005 |
| WO | 2006040307 A1 | 4/2006 |
| WO | 2006045042 A1 | 4/2006 |
| WO | 2006046950 A1 | 5/2006 |
| WO | 2006069078 A2 | 6/2006 |
| WO | 2006081545 | 8/2006 |
| WO | 2006084165 A2 | 8/2006 |
| WO | 2006084166 A2 | 8/2006 |
| WO | 2006108145 A1 | 10/2006 |
| WO | 2006108964 A2 | 10/2006 |
| WO | 200713465 A1 | 2/2007 |
| WO | 2007059199 A2 | 5/2007 |
| WO | WO 2007/059199 * | 5/2007 |
| WO | 2007087190 A2 | 8/2007 |
| WO | 2007097994 A2 | 8/2007 |
| WO | 2007149348 A2 | 12/2007 |
| WO | 2008033950 A2 | 3/2008 |
| WO | 2008065467 A1 | 6/2008 |
| WO | 2009064866 A1 | 5/2009 |

OTHER PUBLICATIONS

PCT/US2008/083381 filed Nov. 13, 2008 Written Opinion of the International Searching Authority dated Dec. 29, 2008.

U.S. Appl. No. 12/269,749, filed Nov. 12, 2008 Non-Final Office Action dated Sep. 14, 2011.

U.S. Appl. No. 12/269,749, filed Nov. 12, 2008 Notice of Allowance dated Mar. 16, 2012.

AU 2006332514 filed Dec. 28, 2006 First Examiner's Report dated Oct. 4, 2011.

AU 2006332514 filed Dec. 28, 2006 Second Examiner's Report dated Jul. 5, 2012.

AU 2013203711 filed Apr. 11, 2013 Examination Report No. 1 dated May 10, 2013.

BARD (Article), "Avaulta™ BioSynthetic Support System," http://www.crbard.com/news/innovations/Avaulta.cfm (2007).

BARD (Article), "AVAULT™ Bio-Synthetic Support System 'Anterior and Posterior Posterior Pelvic Floor Defect Repair with the Avaulta™ Bio-synthetic Support system,'" http://www.bardmdu.com/products/loadProduct.aspx?prodID=280&bUnitID=3 (2007).

BARD (Article), "PelviLace® to Trans-Obturator BioUrethral Support System," http://www.bardurological.com/products/loadproduct.aspx?prodID=277 (2008).

BARD (Article), "URETEX® TO—Trans-Obturator Urethral Support System 'Not all Mesh is created equal,'" Copyright 1997-2004, <http://www.barduroloqical.com/products/loadproductaspx?prodID=186>.

BARD Photo Library "Uretex® Mesh," printed Jul. 12, 2006; http://www.bardurological.com/products/product_photoLibrary.aspx?prodID=185&photoID=269 .

Bard Photo Library, "Avaulta™ Posterior BioSynthetic Support System", Copyright 1997-2008; printed Oct. 23, 2008; http://www.bardurological.com/products/product_photolibrary.aspx?prodID=281&photoID=326>.

Bard Photo Library, Uretex® Mesh in the Anatomy—printed Jul. 12, 2006 <http://www.bardurological.com/products/product_photoLibrary.aspx?prodID=185&photoID=270>.

Bard Photo Library, Hook Introducer 2 printed Jul. 12, 2006 <http://www.bardurological.com/products/product_photoLibrary.aspx?prodID=186&photoID=344>.

(56) References Cited

OTHER PUBLICATIONS

Bard Photo Library, Hook Introducer printed Jul. 12, 2006 http://www.bardurological.com/products/product_photoLibrary.aspx?prodID=186&photoID=343.
Bard Photo Library, Pelvic Diagram 1 (photo id 282) printed Jul. 12, 2006 http://www.bardurological.com/products/product_photoLibrary.aspx?prodID=186&photoID=282.
Bard Photo Library, Pelvic Diagram 2 (photo id 283) printed Jul. 12, 2006 http://www.bardurological.com/products/product_photoLibrary.aspx?prodID=186&photoID=283.
Bard Photo Library, Pelvic Diagram 3 (photo id 284) printed Jul. 12, 2006 http://www.bardurological.com/products/product_photoLibrary.aspx?prodID=186&photoID=284.
BARD Photo Library, Pelvic Diagram 4 (photo id 285) printed Jul. 12, 2006 http://www.bardurological.com/products/product_photoLibrary.aspx?prodID=186&photoID=285.
BARD Photo Library, Surgical Technique (photo id 336) printed Jul. 12, 2006 http://www.bardurological.com/products/product_photoLibrary.aspx?prodID=186&photoID=336.
BARD Photo Library, Surgical Techniques (photo id 337) printed on Jul. 12, 2006 http://www.bardurological.com/products/product_photoLibrary.aspx?prodID=186&photoID=337.
BARD Photo Library, Surgical Techniques (photo id 338) printed Jul. 12, 2006 http://www.bardurological.com/products/product_photoLibrary.aspx?prodID=186&photoID=338.
BARD Photo Library, Surgical Techniques (photo id 339) printed Jul. 12, 2006 http://www.bardurological.com/products/product_photoLibrary.aspx?prodID=186&photoID=339.
BARD Photo Library, Surgical Techniques (photo id 340) printed Jul. 12, 2006 http://www.bardurological.com/products/product_photoLibrary.aspx?prodID=186&photoID=340.
BARD Photo Library, Surgical Techniques (photo id 341) printed Jul. 12, 2006 http://www.bardurological.com/products/product_photoLibrary.aspx?prodID=186&photoID=341.
BARD Photo Library, Surgical Techniques (photo id 345) printed Jul. 12, 2006 http://www.bardurological.com/products/product_photoLibrary.aspx?prodID=186&photoID=345.
BARD Photo Library, Uretex T.O. Transobturator Urethral Support System printed Jul. 12, 2006 <http://www.bardurological.com/products/product_photoLibrary_aspx?productID=186&photoID=266>.
BARD Photo Library, Uretex® TO Trans-Obturator Urethral Support System dated Oct. 23, 2008<http://www.bardurological.com/products/product_photoLibrary.aspx?prodID=186&photoID=204&bUnitID=2>.
BARD Photo Library, Urethral Mesh printed Jul. 12, 2006 <http://www.bardurological.com/products/product_photoLibrary.aspx?prodID=185&photoID=271>.
BARD, "Avaulta™ Anterior BioSynthectic Support System," Copyright 2006-2011, http://www.bardnordic.com/main/product.asp?.sectionTypeID=2&sectionID=6&productID=247.
BARD, "Uretex® Self-Anchoring Urethral Support System—FAQ," printed Jul. 12, 2006; <http://www.bardurological.com/products/product_faq.aspx?prodID=185>.
Bryans, Fred E. "Marlex gauze hammock sling operation with Cooper's ligament attachment in the management of recurrent urinary stress incontinence." American Journal of Obstetrics and Gynecology, vol. 133, No. 3, Feb. 1979.
Burch, John C., "Urethrovaginal fixation to Cooper's ligament for correction of stress incontinence, cystocele, and prolapse," Am. J. Obst. & Gyne, 281-290 (1961).
Burch, John C.; "Urethrovaginal fixation to Cooper's ligament for correction of stress incontinence, cystocele, and prolapse." American Journal of Obstetrics & Gynecology, vol. 31, No. 2, Feb. 1961, pp. 281-290.
Choe, JM, "Preventing urethral obstruction using the 6-point fixation and weight-adjusted spacing nomogram during sling surgery," Int Urogynecol J Pelvic Floor Dysfunct, 2001;12(2):122-8.
Choe, Jong M., Staskin, David R.; "Gore-Tex Patch Sling: 7 Years Later"; Adult Urology, 54(4), pp. 641-646, 1999.

CN 200880115957.3 filed May 12, 2010 Office Action dated Apr. 28, 2012.
CN 200880115957.3 filed May 12, 2010 Office Action dated Dec. 12, 2012.
Collinet, P., et al., "Cure de cystocele par plastron vaginal," J Gynecol Obstet Biol Reprod, 29:197-201 (2000).
Cook Medical, Needle Suspension Product Pages, <<http://www.cookmedical.com>>, last accessed Aug. 13, 2008.
Cook; Urogynecology; Product Technical Datasheet and Order form. 1996.
Cosson, M., et al., "Cure of cystocele with vaginal patch," Prog Urol. Apr. 2001;11(2):340-6.
Cosson, M., et al., "The vaginal patch plastron for vaginal cure of cystocele. Preliminary results for 47 patients," Eur J Obstet Gynecol Reprod Giol. 2001, March;95(1):73-80.
Cosson, Michel, et al., "Cure de cystocele par plastron vaginal," Progres en Urologie, 11:340-346 (2001).
Cruikshank, Stephen H., et al., "Anterior vaginal wall culdeplasty at vaginal hysterectomy to prevent posthysterectomy anterior vaginal wall prolapse," Am. J. Obstet. Gynecol., 1863-1872 (1996).
De Leval J., "Novel surgical technique for the treatment of female stress urinary incontinence: transobturator vaginal tape inside-out," Eur Urol. Dec. 2003;44(6):724-30.
Delorme, E., "Transobturator urethral suspension: mini-invasive procedure in the treatment of stress urinary incontinence in women," Prog Urol. Dec. 2001;11(6):1306-13.
Delorme, E., et al., "Transobturator tape (Uratape). A new minimally invasive method in the treatment of urinary incontinence continence in women," Prog Urol. Sep. 2003;13(4):656-9.
Delorme, Emmanuel., "Transobturator urethral suspension: mini-invasive procedure in the treatment of stress urinary incontinence in women," Progress in Urology, 11(6):1306-13, Dec. 2001.
Di Benedetto, V., et al., "Transurethral Puncture of Ureterocele Associated With Single Collecting System in Neonates," J. Ped. Surg., 32: 1325-1327, 1997.
Dmochowski et al., "Biocompatibility Assessment of Synthetic Sling Materials for Female Stress Urinary Incontinence," The Journal of Urology, vol. 178, Issue 4, pp. 1171-1181, Oct. 2007.
Dmochowski et al., "Erosion of Woven Polyester Pubovaginal Sling," The Journal of Urology, vol. 162, Issue 6, pp. 2070-2072, Dec. 1999.
Dmochowski, R., et al., "The Protegen Sling for the Treatment of Female Stress Urinary Incontinence," J. Urol., http://home.satx.rr.com/sgsu/usurg/protegen.html (1997).
Miklos et al., Laparoscopic Urogynecology Center of Atlanta-Dr. Miklos & Dr. Moore, "Laparoscopic and Minimally Invasive Procedures, 'Tension Free Vaginal Tape (TVT) Sling'" printed Jul. 12, 2006; <http://www.urogynecologychannel.net/lap_proc12.php>.
Miklos et al., Vaginal prolapse relaxation and enterocele repair, printed Jul. 12, 2006; http://www.urogynecologychannel.net/prolapse6.php.
Miklos et al., Vaginal prolapse relaxation, posterior vaginal wall prolapse, printed Jul. 12, 2006; http://www.urogynecologychannel.net/prolapse3.php.
Miklos et al., Vaginal prolapse relaxation, uterine prolapse, printed Jul. 12, 2006; <http://www.urogynecologychannel.net/prolapse4.php>.
Miklos et al., Vaginal prolapse relaxation, uterosacral ligaments, printed Jul. 12, 2006; http://www.urogynecologychannel>.net/prolapse2a.php.
Miklos et al., Vaginal prolapse relaxation, vaginal vault prolapse, printed Jul. 12, 2006; <http://www.urogynecologychannel.net/prolapse5.php>.
Miklos et al., Vaginal relaxation, vaginal prolapse relaxaton, enterocele repair, Types of Vaginal Prolapse, printed on Jul. 12, 2006, http://www.urogyneocologychannel.net/prolapse.php?id=Prolapse.
Moore, Robert D., "Transobturator Approach for Cystocele Repair With Anterior Wall Mesh," <http://www.obgyn.net/hysterectomy-alternatives/hysterectomy-alternatives.asp>? page=urogyn/articles/moore_cystocele (2006).
Morgan, J.E.; "A sling operation, using Marlex polypropylene mesh, for treatment of recurrent strss incontinence." vol. 106, No. 3, pp. 369-377, Feb. 1970.

(56) References Cited

OTHER PUBLICATIONS

Mubiayi N et al. "Surgical cure of stress urinary incontinence with vaginal tissue sling: technique, results, indications," Prog Urol. Feb. 2002;12(1):60-9.
MX/a/2010/005271 Office Action dated Mar. 7, 2013.
Narik, G., Palmrich, A.H.; "A simplified sling operation suitable for routine use"; American Journal of Obstetrics & Gynecology, vol. 84, No. 3, Aug. 1962.
Netterimages.com, "Cystocele, Urethrocele," Image No. 5192, printed Jul. 24, 2006; <http://ww.netterimages.com/images/vpv/000/000/005/5192-05>.
Netterimages.com, "Rectocele, Enterocele," Image No. 5193, printed Jul. 24, 2006; <http://www.netterimages.com/image/5193.htm>.
Nguyen, JK, "Current concepts in the diagnosis and surgical repair of anterior vaginal prolapse due to paravaginal defects," Obstet Gynecol Surv, Apr. 2001;56(4):239-46.
Nichols, David H.; "The Mersilene Mesh Gauze-Hammock for Severe Urinary Stress Incontinence"; Obstetrics and Gynecology; Obstetrics & Gynegology, vol. 41, No. 1, pp. 88-93, Jan. 1973.
Nickel, RF, et al, "Evaluation of a transpelvic sling procedure with and without colposuspension for treatment of female dogs with refractory urethral sphincter mechanism incompetence." Vet Surg. Mar.-Apr. 1998;27(2):94-104.
Norris, Jeffrey P., Breslin, David S., Staskin, David R.; "Use of Synthetic Material in Sling Surgery: A Minimally Invasive Approach"; Journal of Endourology; vol. 10, No. 3, Jun. 1996.
O'Donnell, Pat D.; "Combined Raz Urethral Suspension and McGuire Pubovaginal Sling for Treatment of Complicated Stress Urinary Incontinence"; Journal of the Arkansas Medical Society, vol. 88, No. 8, pp. 389-392, Jan. 1992.
Okoshi, Takafumi, et al., "Long-term Results of a New Antithrombogenic Cardiac Wall Substitute," Trans Am Soc. Artif Intern Organs, XXXV:391-395 (1989).
Parra, O. et al., "Experience with a Simplified Technique for the Treatment of Female Urinary Incontinence," the British Journal of Urology (1990), 66, 615-617.
PCT/AU2000/001298 filed Oct. 20, 2000 International Preliminary Examination Report dated Jan. 29, 2002.
PCT/AU2000/001298 filed Oct. 20, 2000 Search Report dated Jan. 3, 2001.
PCT/US03/24212 filed Aug. 1, 2003 International Search Report dated May 28, 2004.
PCT/US03/24212 filed Aug. 1, 2003 Written Opinion dated Aug. 24, 2004.
PCT/US07/78308 filed Sep. 12, 2007 International Search Report dated Jun. 5, 2008.
PCT/US07/78308 filed Sep. 12, 2007 Written Opinion dated Jun. 5, 2008.
PCT/US2003/013113 filed Apr. 28, 2003 International Preliminary Examination Report dated Oct. 14, 2004.
PCT/US2003/013113 filed Apr. 28, 2003 International Seach Report dated Oct. 15, 2003.
PCT/US2003/024212 filed Aug. 1, 2003 International Search Report dated May 24, 2004.
PCT/US2003/024212 filed Aug. 1, 2003 Written Opinion dated Aug. 24, 2004.
PCT/US2006/030369 filed Aug. 3, 2006 International Preliminary Report on Patentability dated Mar. 31, 2009.
PCT/US2006/030369 filed Aug. 3, 2006 Search Report dated Aug. 12, 2008.
PCT/US2006/030369 filed Aug. 3, 2006 Written Opinion dated Aug. 12, 2008.
PCT/US2006/030370 filed Aug. 3, 2006 International Preliminary Report on Patentability dated Feb. 4, 2008.
PCT/US2006/030370 filed Aug. 3, 2006 Search Report dated Jul. 20, 2007.
PCT/US2006/030370 filed Aug. 3, 2006 Written Opinion dated Jul. 20, 2007.
PCT/US2006/030581 filed Aug. 3, 2006 International Preliminary Report on Patentability dated Mar. 17, 2009.
PCT/US2006/030581 filed Aug. 3, 2006 Search Report dated Jul. 7, 2008.
PCT/US2006/030581 filed Aug. 3, 2006 Written Opinion dated Jul. 7, 2008.
PCT/US2006/044315 filed Nov. 14, 2006 International Preliminary Report on Patentability dated Mar. 24, 2009.
PCT/US2006/044315 filed Nov. 14, 2006 International Seach Report dated May 6, 2008.
PCT/US2006/044315 filed Nov. 14, 2006 Written Opinion dated May 6, 2008.
PCT/US2006/062639 filed Dec. 28, 2006 International Preliminary Report on Patentability dated Oct. 7, 2008.
PCT/US2006/062639 filed Dec. 28, 2006 Search Report dated Oct. 1, 2007.
PCT/US2006/062639 filed Dec. 28, 2006 Written Opinion dated Oct. 1, 2007.
PCT/US2007/006461 filed on Mar. 15, 2007 International Preliminary Report on Patentability dated Sep. 16, 2008.
PCT/US2007/006461 filed on Mar. 15, 2007 Search Report dated May 22, 2008.
PCT/US2007/006461 filed on Mar. 15, 2007 Written Opinion dated May 22, 2008.
Pelosi, MA, et al., "The transobturator sling: newest tension-free suburethral sling for treatment of stress urinary incontinence," Surg Technol Int. 2004;13:173-9. Review.
Eglin, G., et al., "Transobturator subvesical mesh. Tolerance and short-term results of a 103 case continuous series," Gynecology Obstetrique & Fertilite, Jan. 2003;31(1):14-19(6).
EP 03751825.5 Supplementary European Search Report dated Jun. 19, 2009.
EP 06789465.9 filed Aug. 3, 2006 Search Report dated Apr. 28, 2010.
EP 06800736.8 filed Aug. 3, 2006 Examination Report dated Feb. 24, 2012.
EP 06800736.8 filed Aug. 3, 2006 Search Report dated Apr. 26, 2010.
EP 06800736.8 Summons to attend oral proceedings dated Jan. 22, 2013.
EP 06824802.0 filed Aug. 3, 2006 Search Report dated Dec. 13, 2010.
EP 06827826.6 filed May 14, 2008 Supplementary Search Report dated Feb. 4, 2011.
EP 06846828.9 filed Dec. 28, 2006 Office Action dated May 18, 2010.
EP 06846828.9 filed Dec. 28, 2006 Official Minutes dated Oct. 12, 2012.
EP 06846828.9 filed Dec. 28, 2006 Search Report dated Apr. 26, 2010.
EP 07753112.7 filed Mar. 15, 2007 Supplemental European Search Report dated Dec. 30, 2010.
EP 08849041.2 extended European Search Report dated Mar. 12, 2013.
Falconer, C., Ekman-Ordeberg, G., Malmstrom, A., Ulmsten, U.; "Clinical Outcome and Changes in Connective Tissue Metabolism After Intravaginal Slingplasty in Stress Incontinent Women"; The International Urogynecology Journal; vol. 7, pp. 133-137, 1996.
Falconer, C., Soderberg, M., Blomgren, B., Ulmsten, U.; "Influence of Different Sling Materials on Connective Tissue Metabolism in Stress Urinary Incontinent Women"; The International Urogynecology Journal; S19-S23, 2001.
Ghoniem, Gamal et al., "Modified Pubovaginal Sling and Martius Graft for Report of the Recurrent Vesicovaginal Fistula Involving the Internal Urinary Sphincter," Eur Urol 1995; 27:241-245.
Glowacki, CA, et al., "Bone anchors in urogynecology," Clin Obstet Gynecol, Sep. 2000;43(3):659-69, Review.
Gomelsky, Alex, et al., "Biocompatibility Assessment of Synthetic Sling Materials for Female Stress Urinary Incontinence," The Journal of Urology, Oct. 2007, vol. 178, pp. 1171-1181.
Gormley, E. Ann et al., "Pubovaginal slings for the management of urinary incontinence in female adolescents," The Journal of Urology, vol. 152, pp. 822-825, Aug. 1994.
Horbach, Nicolette S.; "Suburethral Sling Procedures"; Urogynecology and Urodynamics Theory and Practice Fourth Edition; Chapter 42, pp. 569-579, 1996.

(56) References Cited

OTHER PUBLICATIONS

Image, <http://www.ivstunneller.com/images/anterior-procedure.jpg>printed on Jul. 10, 2006.
Image, www.obgyn.neUurogyn/articles/moore_cystocele , printed Jul. 10, 2006 and Mar. 10, 2011, <http://www.obgyn.neUurogyn/articles/moore_cystocele>.
Iosif, S., et al., "Urodynamic studies of women with prolapse and stress incontinence before and after surgical repair," Urodynamics Studies, 101:1433-1442 (1979).
Jacquetin B., "Bladder suspension exclusively through the vagina: at last!" J Gynecol Obstet Biol Reprod 1991;20 (8):1143-4, Paris.
Jacquetin B., "Genital prolapses. Diagnosis," Rev Prat. Sep. 15, 2001;51(14):1609-16.
Jacquetin B., "Use of "TVT" in surgery for female urinary incontinence," J Gynecol Obstet Biol Reprod, May 2000;29(3):242-7.
Johnson & Johnson (Article), "Gynecare Prolift Systems: 'You Know Where You Want to Go . . . GPS for Pelvic Floor Repair,'" <http://www.jnjgateway.com/home.jhtml?loc=USENG&page=viewContent&contentId=09008b98>8102f39b&parentId=09008b988102f39b (2006).
Johnson & Johnson Gateway®, "Optimal technique for access to anatomic landmarks," <http://www.jnjgateway.com/home.jhtml?loc=USENG&page=viewContent&contentID=090> (2005).
Johnson & Johnson Gateway®: Gynecare Prolift Innovative Design, http://www.jnjgateway.com/home.jhtml?loc=USENG&page=viewContent&contentID=090 (2005).
Johnson & Johnson Gateway®: Gynecare TVT Abdominal Approach, <http://www.jnjgateway.com/home.jhtml?loc=USENG&page=vieewContent&contentID=090> (2005).
Johnson & Johnson Gateway®: Gynecare TVT Obturator System, "Tension-Free Support for Incontinence" <http://www.jnjgateway.com/home.jhtml?loc=USENG&page=viewContent&contentID=090> (2005).
Johnson & Johnson Gateway®: Vaginal Approach, <http://www.jnjgateway.com/home.jhtml?loc=USENG&page=viewContent&contentID=090> (2005).
JP 2008-525210 filed Feb. 1, 2008 Office Action dated Oct. 5, 2011.
JP 2008-525211 filed Feb. 1, 2008 Office Action dated Oct. 31, 2011.
JP 2008-525252 filed Aug. 3, 2006 Office Action dated Aug. 26, 2011.
JP 2008-525252 filed Aug. 3, 2006 Office Action dated May 11, 2012.
JP 2008-548841 filed Jun. 27, 2008 Office Action dated Jan. 19, 2012.
JP 2008-548841 filed Jun. 27, 2008 Office Action dated Nov. 28, 2012.
Karlovsky, Matthew E., et al., "Surgical Treatment of Stress Urinary Incontinence", Journal of Urology, 2003.
Karmarkar, Santoshi J., et al., "The 3-loop technique: A reliable technique for anterior pubic fixation in bladder exstrophy," The Journal of Urology, Sep. 1995 vol. 154, 1173-1176.
Karram, Mickey M., Bhatia, Narender N.; "Patch procedure: Modified Transvaginal Fascia Lata Sling for recurrent or severe stress urinary incontinence"; Obstetrics and Gynecology, pp. 461-463, Mar. 1990.
Kelly, Mark J. et al., "Symptom analysis of patients undergoing modified Pereyra bladder neck suspension for urinary stress incontinence," Urology, vol. 37, No. 3, Mar. 1991.
Kersey, J., "The guaze hammock sling operation in the treatment of stress incontinence," British Journal of Obstetrics and Gynaecology, vol. 90, pp. 945-949, Oct. 1983.
Kil, P.J.M. et al., "Transvaginal ultrasonography and urodynamic evaluation after suspension operations: comparison among the Gittles, Stamey and Burch suspensions," The Journal of Urology, vol. 146, pp. 132-136, Jul. 1991.
Kobashi, Kathleen C., et al., "Erosion of Woven Polyester Pubovaginal Sling," The Journal of Urology, Dec. 1999, vol. 162, pp. 2070-2072.
Korda, Andrew; Peat, Brian; Hunter, Peter; "Experience with Silastic Slings for Female Urinary Incontinence"; Aust NZ J Obstet Gynaecol, pp. 150-154, 1989.

Korman, Howard J. et al., "Success rate of modified Pereyra bladder neck suspension determined by outcomes analysis," The Journal of Urology, vol. 152, pp. 1453-1457, Nov. 1994.
Lichtenstein, Irving L., Shulman, Alex G., Amid, Parviz K., Montllor, Michele M.; "The Tension-Free Hernioplasty"; The American Journal of Surgery, vol. 157; Feb. 1989.
McIndoe, G.A.J., Jones, R.W., Grieve B.W.; "The Aldridge Sling Procedure in the Treatment of Urinary Stress Incontinence"; Aust NZ J Obstet Gynaecol; 1987.
MedlinePlus Medical Encyclopedia, "Female urinary tract," http://www.nlm.nih.gov/medlineplus/ency/imagepages/1122.htm (2004).
Petros, Peter E. Papa et al., "The Combined Intravaginal Sling and Tuck Operation. An Ambulatory Procedure for Cure of Stress and Urge Incontinence," Acta Obstet Gynecol Scan Suppl 153: 53, pp. 115-117, 1990.
Petros, Peter E. Papa, "Ambulatory surgery for urinary incontinence and vaginal prolapse," Med. J. Of Australia, 161:171-172 (1994).
Raz, Shlomo et al., "The Raz Bladder Neck Suspension: Results in 206 Patients," The Journal of Urology, vol. 148, pp. 845-850, Sep. 1992.
Raz, Shlomo; Female Urology; Second Edition; Selected Chapters, © 1996.
Ridley, John H.; "Appraisal of the Goebell-Frangenheim-Stoeckel sling procedure"; American Journal of Obstetrics & Gynecology, vol. 95, No. 5, pp. 714-721, Jul. 1966.
Scotti, RJ, et al., "Paravaginal repair of lateral vaginal wall defects by fixation to the ischial periosteum and obturator membrane," Am J Obstet Gynecol. Dec. 1998;179(6 Pt 1):1436-45.
Shands Healthcare, "Bladder neck is elevated by stitching it and the urethra to anterior pubic bone," Copyright 1997-2011, printed Nov. 3, 2010,<http://www.shands.org/health/imagepages/17202.htm>.
Silver, Richard I., et al., "Staged closure of the pelvis in cloacal exstrophy: first description of a new approach," The Journal of Urology, Jan. 1999, vol. 161, pp. 263-266.
Stanton, Stuart L.; "Suprapubic Approaches for Stress Incontinence in Women"; Journal of the American Geriatrics Society, vol. 38, No. 3, pp. 348-351, Mar. 1990.
Staskin, David R., Choe Jong M., Breslin, David S.; "The Gore-Tex sling procedure for female sphincteric incontinence: indications, technique, and results"; World J. Urol.; vol. 15, pp. 295-299, 1997.
Sussman, J.S., et al., "A Comparison of Methods of Repairing the Symphysis Pubis in Bladder Exstrophy by Tensile Testing," Brit. J. Urol., 79: 979-984, 1997.
Ulmsten, U. et al., "An Ambulatory Surgical Procedure Under Local Anesthesia for Treatment of Female Urinary Incontinence," Int Urogynecol J (1996) 7:81-86.
U.S. Appl. No. 10/633,254, filed Aug. 1, 2003 Advisory Action dated Aug. 26, 2008.
U.S. Appl. No. 10/633,254, filed Aug. 1, 2003 Decision on Appeal dated Jul. 20, 2011.
U.S. Appl. No. 10/633,254, filed Aug. 1, 2003 Final Office Action dated Jun. 18, 2008.
U.S. Appl. No. 10/633,254, filed Aug. 1, 2003 Non-Final Office Action dated Jan. 29, 2007.
U.S. Appl. No. 10/633,254, filed Aug. 1, 2003 Non-Final Office Action dated Nov. 15, 2005.
U.S. Appl. No. 10/633,254, filed Aug. 1, 2003 Non-Final Office Action dated Sep. 18, 2007.
U.S. Appl. No. 10/633,254, filed Aug. 1, 2003 Notice of Allowance dated Oct. 11, 2011.
U.S. Appl. No. 11/993,003, filed Jan. 22, 2008, Examiner's Answer dated Nov. 30, 2011.
U.S. Appl. No. 11/993,003, filed Jan. 22, 2008 Non-Final Office Action dated Jul. 20, 2011.
U.S. Appl. No. 11/993,089, filed Jun. 9, 2010 Non-Final Office Action dated Aug. 27, 2012.
U.S. Appl. No. 11/993,375, filed Feb. 6, 2009 Non-Final Office Action dated May 10, 2011.
U.S. Appl. No. 11/993,003, filed Jan. 22, 2008 Advisory Action dated Feb. 8, 2011.
U.S. Appl. No. 11/993,003, filed Jan. 22, 2008 Examiner's Answer dated Nov. 30, 2011.

(56) References Cited

OTHER PUBLICATIONS

U.S. Appl. No. 11/993,003, filed Jan. 22, 2008 Final Office Action dated Dec. 10, 2010.
U.S. Appl. No. 11/993,003, filed Jan. 22, 2008 Non-Final Office Action dated Jul. 14, 2010.
U.S. Appl. No. 12/093,493, filed Jul. 14, 2008 Final Office Action dated Jul. 6, 2011.
U.S. Appl. No. 12/093,493, filed Jul. 14, 2008 Non-Final Office Action dated Jan. 20, 2011.
U.S. Appl. No. 12/093,493, filed Jul. 14, 2008 Notice of Allowability dated Sep. 22, 2011.
U.S. Appl. No. 12/159,589, filed Aug. 15, 2008 Examiner's Answer dated Nov. 9, 2011.
U.S. Appl. No. 12/159,589, filed Aug. 15, 2008 Final Office Action dated May 12, 2011.
U.S. Appl. No. 12/159,589, filed Aug. 15, 2008 Non-Final Office Action dated Dec. 10, 2010.
U.S. Appl. No. 12/159,589, filed Aug. 15, 2008 Non-Final Office Action dated Jul. 12, 2010.
U.S. Appl. No. 12/159,589, filed Aug. 15, 2008 Notice of Panel Decision dated Aug. 29, 2011.
U.S. Appl. No. 12/282,641, filed Dec. 4, 2008 Non-Final Office Action dated Dec. 8, 2011.
U.S. Appl. No. 12/282,641, filed Dec. 4, 2008, Non-Final Office Action dated Jul. 12, 2012.
U.S. Appl. No. 12/441,123, filed May 24, 2010 Advisory Action dated Dec. 7, 2012.
U.S. Appl. No. 12/441,123, filed May 24, 2010 Final Office Action dated Sep. 14, 2012.
U.S. Appl. No. 12/441,123, filed May 24, 2010 Non-Final Office Action dated Apr. 9, 2012.
Wahle, Gregory R. et al., "Vaginal Surgery for Stress Urinary Incontinence," Urology, vol. 43, No. 4, pp. 416-419, Apr. 1994.
Wall, LL, et al., Use of a pedicled rectus abdominus muscle flap sling in the treatment of complicated stress urinary incontinence. Am J Obstet Gynecol. Dec. 1996;175(6):1460-4; Discussion 1464-6.
Walters, Mark D., et al., "Anterior vaginal wall prolapse: Innovative surgical approaches," Cleveland Clinic Journal of Medicine, Dec. 2005, 72:4 S20-S27.
Walters, Mark D., Percutaneous Suburethral Slings: State of the Art, presented at the conference of the American Urogynecologic Society, Chicago (Oct. 2001).
Yan, A., et al, "Cystocele repair by a synthetic vaginal mesh secured anteriorly through the obturator foramen," Eur J Obstet Gynecol Reprod Biol, Jul. 15, 2004;115(1):90-4.
Zimmern, Philippe, et al., "A prospective evaluation of four-corner bladder neck suspension for grade II/III cystocele repair," Urodynamics Soc. Symp. Abstracts, p. 231 (1990).

\* cited by examiner

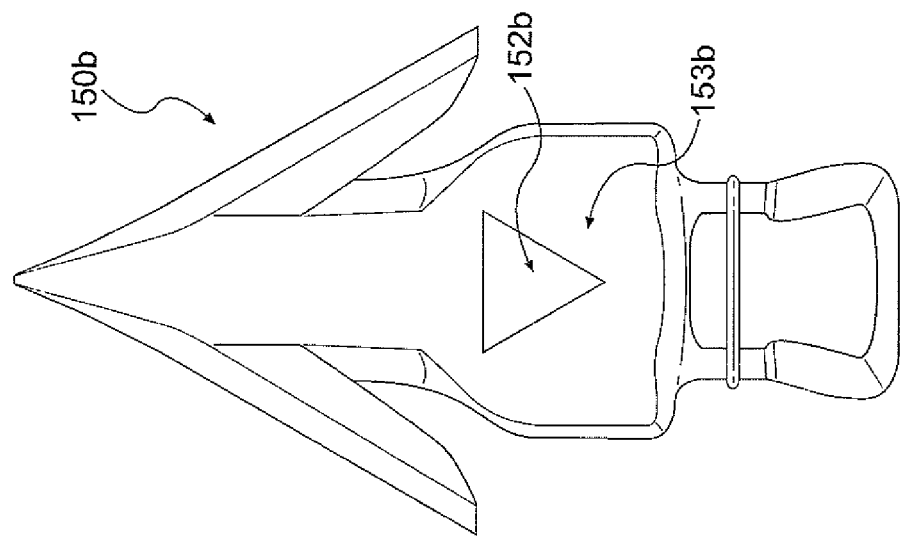
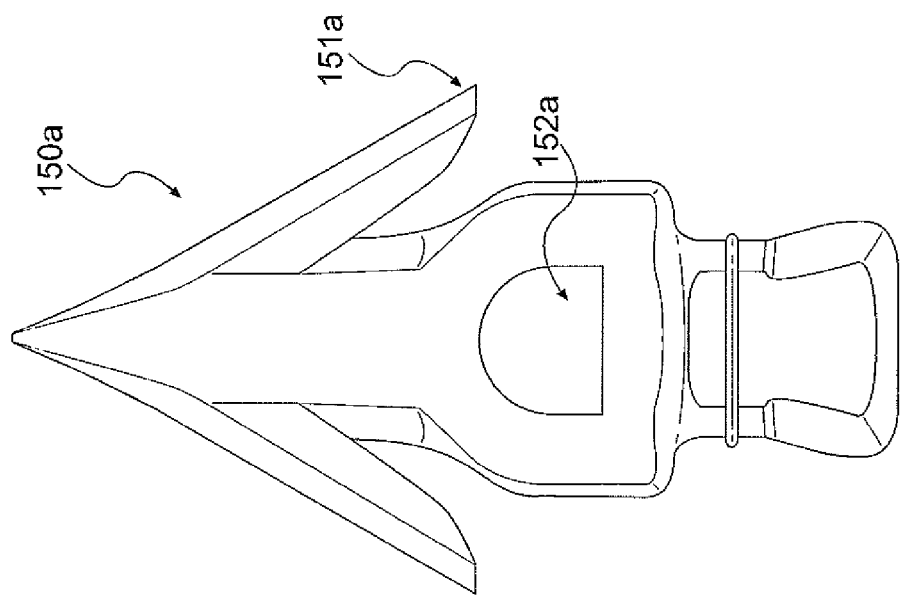

ADJUSTABLE TISSUE SUPPORT MEMBER

This application is a continuation of U.S. patent application Ser. No. 12/269,749, filed Nov. 12, 2008, now U.S. Pat. No. 8,206,280, which claims the benefit of priority to U.S. Provisional Application Nos. 60/987,469, filed Nov. 13, 2007, titled "Implant with Adjustability Feature;" 61/015,741, filed Dec. 21, 2007, titled "Tissue Anchor Insertion Device;" 61/020,231 filed Jan. 10, 2008, titled "Continuous Knit Tubular Mesh Implant;" 61/025,461 filed Feb. 1, 2008, titled "Adjustable Tissue Support Member;" and 61/102,147, filed Oct. 2, 2008, titled "Adjustable Tissue Support Member," the disclosures of which are all incorporated herein by reference in their entirety.

Female urinary incontinence is commonly treated by a sling suspension procedure. Generally, sling suspension procedures involve the placement of a sling member beneath a patient's urethra. The sling member is suitably implanted in the patient's tissue with an introducer needle, which helps draw the sling into position.

Slings have been made of numerous materials, synthetic and natural, and are generally in the form of a mesh. A traditional sling procedure involves placing a strip of implant material (natural tissue, synthetic mesh, or a combination of the two) under the urethra and securing it to the rectus fascia or other portions of the patient's anatomy with sutures to hold the implant in position during the healing process.

Improved techniques have been developed that speed the implant process by reducing the number of incisions made and by altering the pathways by which the implant is introduced into the body. These improvements, which employ specialized instrumentation, help to reduce operative time and have made the procedure less invasive. The improved techniques generally require that an implant be joined to an introducer needle. The implant is then inserted into, and pulled through, the body. Subsequently, the implant is detached from the introducer needle.

Such procedures may require long needle passes and substantial tissue dissection, such as in the case of a retropubic or suprapubic procedure. Long needle passes increase the likelihood of an unintended perforation of a body structure (e.g., the bladder). In addition, the procedures typically require not only at least one vaginal incision, but also two external incisions at the locus of the obturator foramina in the case of a transobturator approach, and above the pubic bone in the retro- and suprapubic approaches.

Such procedures often use instrumentation that lacks an adjustability feature. A mesh sling has to exert an appropriate amount of tension on the urethra. Excessive tension can result in kinking of the urethra and/or undue tissue erosion, whereas insufficient tension can result in an ineffective sling. It might be desirable to be able to adjust the tension of the sling after both ends of the sling have been anchored in tissue, but before the tension is fixed and surgery is concluded. In addition, it could be desirable to provide bi-directional adjustment and not just adjustment in a single direction. Features that further the achievement of at least one of the foregoing goals could be desirable.

In view of the above, it would be beneficial to have a minimally invasive sling suitable for treating various conditions, such as incontinence, for example fecal and urinary incontinence, such as female urinary incontinence. According to various embodiments, each end of the implanted minimally invasive sling terminates in a tissue anchor. The length of the sling (and the tension exerted by the sling on the urethra) is configured for adjustment once at least one of the tissue anchors has been implanted.

SUMMARY

According to one embodiment, there is disclosed herein a tissue support system comprising an implantable tissue support member, wherein the implantable tissue support member comprises a tissue support portion having a length and a width, a first arm disposed at one end of the tissue support portion, and a second arm disposed at an opposite end of the tissue support portion, a first tissue anchor connected to the first arm, and a second tissue anchor connected to the second arm, wherein the second tissue anchor is slideable along a length of said second arm.

According to another embodiment, there is disclosed herein a tissue support system comprising an implantable tissue support member, wherein the implantable tissue support member comprises a tissue support portion having a first end and a second end, a first arm having a first end and a second end, wherein the first end is joined to the first end of the tissue support portion, a second arm having a first end and a second end, wherein the first end is joined to the second end of the tissue support portion, a first tissue anchor fixed to the second end of the first arm, and a second tissue anchor having an aperture therein, wherein the aperture is configured to at least partially enclose a portion of the second arm.

According to yet another embodiment, there is disclosed herein a method for providing support to body tissue, comprising making an incision in the vaginal wall, inserting an introducer needle having a first tissue anchor at the distal end thereof into the incision in the direction of the obturator membrane, wherein the first introducer needle is connected to an implant, ejecting the first tissue anchor from the introducer needle, withdrawing the introducer needle from the incision, and inserting a second tissue anchor in the distal end thereof wherein the second tissue anchor is connected to an implant, re-inserting the introducer needle into the incision in the direction of the contra-lateral obturator membrane, ejecting the second tissue anchor from the introducer needle, and applying traction to the implant until the desired amount of tissue support is obtained.

According to another embodiment, there is disclosed herein a medical device configured for implantation in tissue, comprising a lumen formed from a flexible material, at least one tissue anchor having at least one aperture therein, said at least one aperture configured to receive said lumen formed from a flexible material, and an anchor stop disposed in said lumen, wherein said anchor stop is configured to resist movement when urged in one direction within said lumen.

BRIEF DESCRIPTION OF THE DRAWINGS

The disclosed embodiments can be better understood with reference to the following drawings. The components in the drawings are not necessarily to scale.

FIGS. 9A-9B illustrate cut-away views of exemplary tissue anchors.

DESCRIPTION

The following description should be read with reference to the drawings. The drawings, which are not necessarily to scale, depict selected embodiments and are not intended to limit the scope of the invention.

Figure 1:
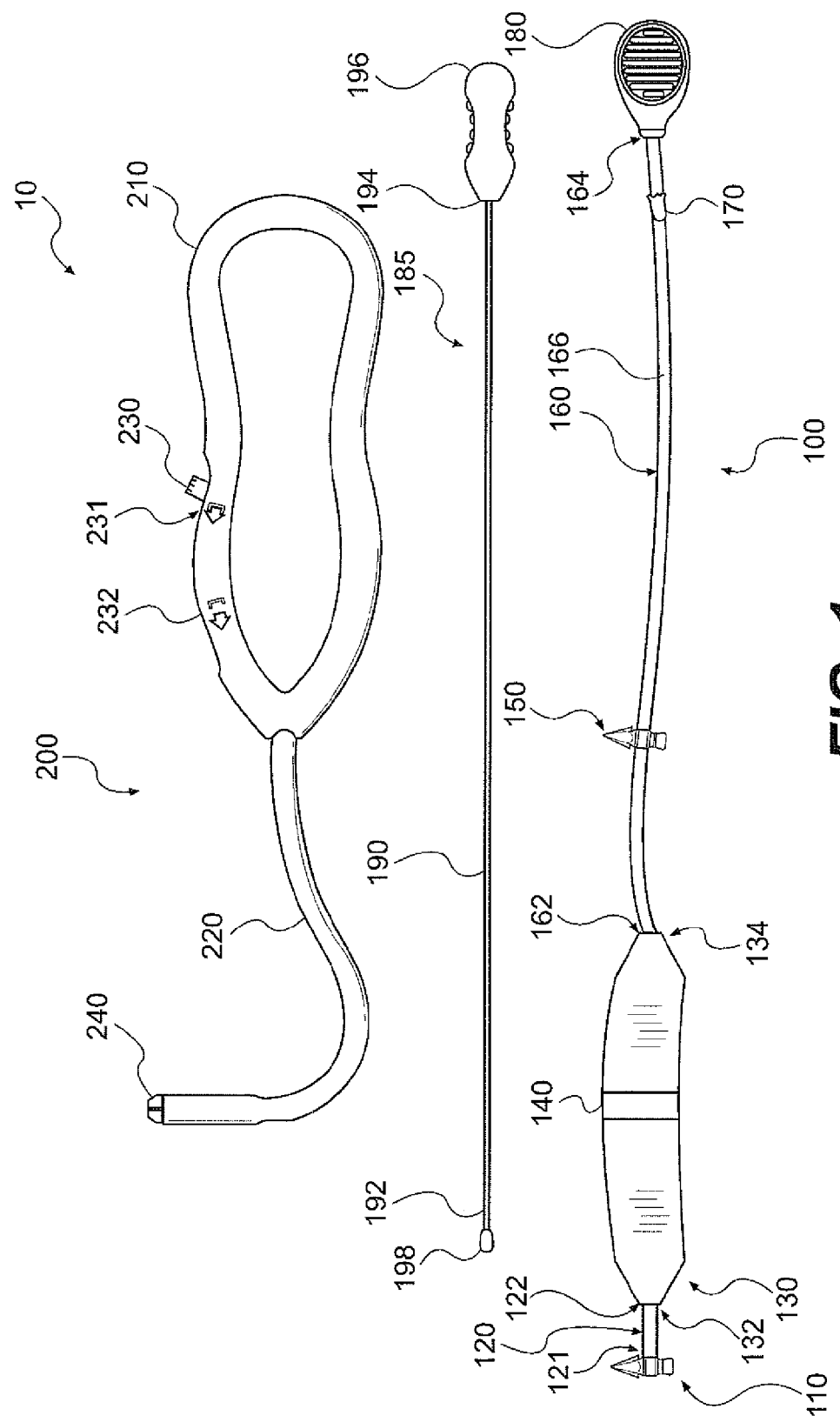
FIG. 1 illustrates one aspect of a tissue support system in accordance with the present disclosure.

FIG. 1 illustrates a tissue support system 10 according to various aspects of the present disclosure. The system includes an implantable tissue support member 100, a stylet 185, and an introducer needle 200. The tissue support member comprises a tissue support portion 130 having ends 132 and 134 connected to arms 120 and 160, and orienting indicia 140. The arm 129 has ends 121 and 122, and arm 160 has ends 162 and 164.

The orienting indicator 140 can comprise, by way of non-limiting example, a dyed centerline, or a colored thread woven into the center portion of the implant. According to one embodiment, the indicator is colored midline indicator in the form of a blue polypropylene thread woven through the middle of tissue support portion 130.

The implantable support member 100 further comprises a first tissue anchor 110, and a second tissue anchor 150. Tissue anchor 150 is configured to be connected to, but moveable along (i.e., slidably attached to), a length of arm 160. According to one embodiment, tissue anchor 150 slides along a length of arm 160. According to various embodiments, tissue anchor 150 has an aperture therein, through which arm 160 is received. According to certain embodiments, anchor 110 is fixed to end 121 of arm 120. According to another embodiment, anchor 110 is configured to be connected to, but moveable along, a length of arm 120.

According to one embodiment, tissue support portion 130 is a flat, single layer of mesh, and arms 120 and 160 are tubular mesh constructs. The tubular knit pattern allows for bi-directional adjustability of the implant once the tissue anchors 110 and 150 are in place. The arms are joined to the support feature via any suitable means, including by stitching, adhesive, sonic welding, and heat-staking. According to one embodiment, each of the arms is sewn to the tissue support portion 130 using the same type and size of polypropylene fiber from which the tissue support portion 130 and arms 120 and 160 are constructed.

According to another embodiment, tissue support portion 130 and arms 120 and 160 are constructed from a unitary tubular member having a single lumen running longitudinally therethrough. In such an embodiment, the diameter of the arms transition at 162 and 122 to form the tissue support portion 130. According to this embodiment, there is no joint at 162 or 122. According to various embodiments, the tubular mesh is smooth, providing a slight "ratcheting" effect during adjustment to give tactile feedback to the user.

Tubular mesh implants can be prepared by a number of known methods. For example, the tubular mesh can be manufactured by circular knitting, either single-ended or double-ended for added strength to provide a stable knit, uniform cross section, and smooth profile. The mesh can be manufactured by weft knitting via a "glove" style knitting machine to make smooth chain link stitches, which can allow diameter variation over a given length. According to another embodiment, the tubular mesh is a double warp knit, providing a high strength, multi-end knit using two flat mesh warp knits that are joined on the sides to make a tube mesh. According to another embodiment, the tubular mesh is made from a flat knitting machine, such as a Shimatronic® flat knitting machine sold by Shima Seiki Mfg., Ltd. of Wakayama, JP.

The mesh portions of implant 100 can have a single-strand or double-strand construction. According to certain embodiments, the tissue support portion 130 is a flat mesh comprising a knitted, open porosity, monofilament, polypropylene mesh strip. The open porosity of the mesh design and large pore sizes allow for macrophage penetration and the creation of an inert scaffold for tissue ingrowth to create a permanent support for the urethra. The pore sizes can be of any suitable diameter to allow tissue ingrowth. The tissue support portion 130 of implant 100 can have smaller pores ranging in diameter from 0.4 mm to 1.1 mm, for example 0.5 mm to 1.0 mm, such as 0.6 to 0.9 mm. The mesh can additionally have larger pores ranging in diameter from 0.8 mm to 1.3 mm, for example 1.0 mm to 1.2 mm.

According to one embodiment, the mesh is a polypropylene knit made from a small diameter fiber to create a soft and pliable material. According to various embodiments, the mesh is constructed so as to avoid, or at least minimize, curling of the implant upon application of a tensile force in the lengthwise direction. According to one embodiment, the mesh implant is a single-knit, double-stranded construction. The fibers can be of any suitable diameter. For example, the fibers can have a diameter ranging from 0.0015" to 0.100", for example 0.002", 0.0025", 0.003" or 0.004".

The implants disclosed herein can be constructed from different types of mesh. One suitable non-limiting example is a knitted polypropylene monofilament mesh fabric, such as BARD MESH from C. R. Bard, Inc. Other materials include SOFT TISSUE PATCH (microporous ePTFE—available from W.L. Gore & Associates, Inc.); SURGIPRO (available from US Surgical, Inc.); TRELEX (available from Meadox Medical); PROLENE and MERSILENE (available from Ethicon, Inc.); and other mesh materials (e.g., available from Atrium Medical Corporation). It is also contemplated that the mesh fabric may be formed from multifilament yarns and that any suitable method, such as knitting, weaving, braiding, molding, and the like, may be employed to form the prosthetic mesh material. The mesh may also be constructed from absorbable materials, such as polylactic acid. According to various embodiments, the mesh implants disclosed herein are manufactured via a knitting machine, such as a computerized Jacquard flat knitting machine.

The implants disclosed herein can include, or be constructed entirely from, a natural material. For example, the natural material can be disposed over at least one surface of the tissue support members disclosed herein. The natural material can be any suitable material including, but not limited to, biologically derived materials, such as cadaveric (human) or xenograft tissue (particularly of porcine or bovine origin)—for example dermis processed to make an acellular collagen scaffold or intestinal submucosa or other biological material and/or bioengineered materials. Collagen materials can be obtained from various sources, such as that available from Cook Biomedical, Inc. under the name COOK SURGISIS soft tissue graft. In one embodiment, the natural material comprises a cross-linked porcine dermal collagen material, such as COLLAMEND surgical implant from Davol (R.I.). Other suitable bioengineered materials may be employed as the present disclosure is not limited in this respect.

The arms 120 and 160 can have any width sufficient for the implant's intended purpose. For example, the arms can have a width ranging from 0.5 to 5.0 mm, including 1 mm to 5 mm, for example 2.0 mm to 4 mm, or 2.5 mm to 3.5 mm. The arms can have a length ranging from 10 mm to 100 mm, for example 20 mm to 60 mm, including 30 mm to 50 mm. According to various embodiments, tissue support portion 130 has a length ranging from about 30 mm to about 100 mm, for example about 40 mm to about 80 mm, including 65 mm. The support portion 130 can have any width sufficient to provide support to a body tissue. According to various embodiments, the width can range from 5 mm to 20 mm, for example 7 mm to 15 mm, including 10 mm to 14 mm. According to one embodiment, the width of tissue support portion 130 ranges from 5 mm to 15 mm, for example 10 mm to 12 mm. According to various embodiments, arms 120 and 160 have the same length, or substantially the same length. According to another embodiment, arms 120 and 160 have different lengths. For example, arm 120 is 5 mm to 20 mm long, for example 80 mm to 15 mm long, and arm 160 is 80 mm to 200 mm, for example 100 mm to 150 mm in length.

According to various embodiments, a tissue anchor can be fixed, either directly or indirectly (i.e., via a connector) to one or both of arms 120 and 160. Any anchor suitable for anchoring an implant to tissue, such as soft tissue, for example muscle tissue, a ligament, a tendon, or a membrane, such as the transobturator membrane, will suffice. The anchor may be fixed to the arms via any suitable means, including mechanically, by adhesive, friction fit, ultrasonic welding, solvent bonding, and heat staking.

According to various embodiments, a first tissue anchor 110 is configured to move freely along a length of arm 120, and a second anchor 150 is also configured to move freely along a length of arm 160. Once the anchors are implanted and the desired tension is obtained, both anchors can be fixed in position to arms 120 and 160. According to another embodiment, a first tissue anchor 110 is permanently fixed to the terminal end 121 of arm 120, and a second anchor 150 is configured to move freely along a length of arm 160. This facilitates the adjustment feature of the implant, such that once the first anchor and then the second anchor are implanted, the tension exerted on the urethra by the sling is adjusted by manipulating arm 160 in either direction relative to the anchor 150. The manipulation is via gripping feature 180, disposed at end 164 of arm 160. Once the desired tension is reached, the arm 160 is fixed in position to the anchor.

Figure 11:
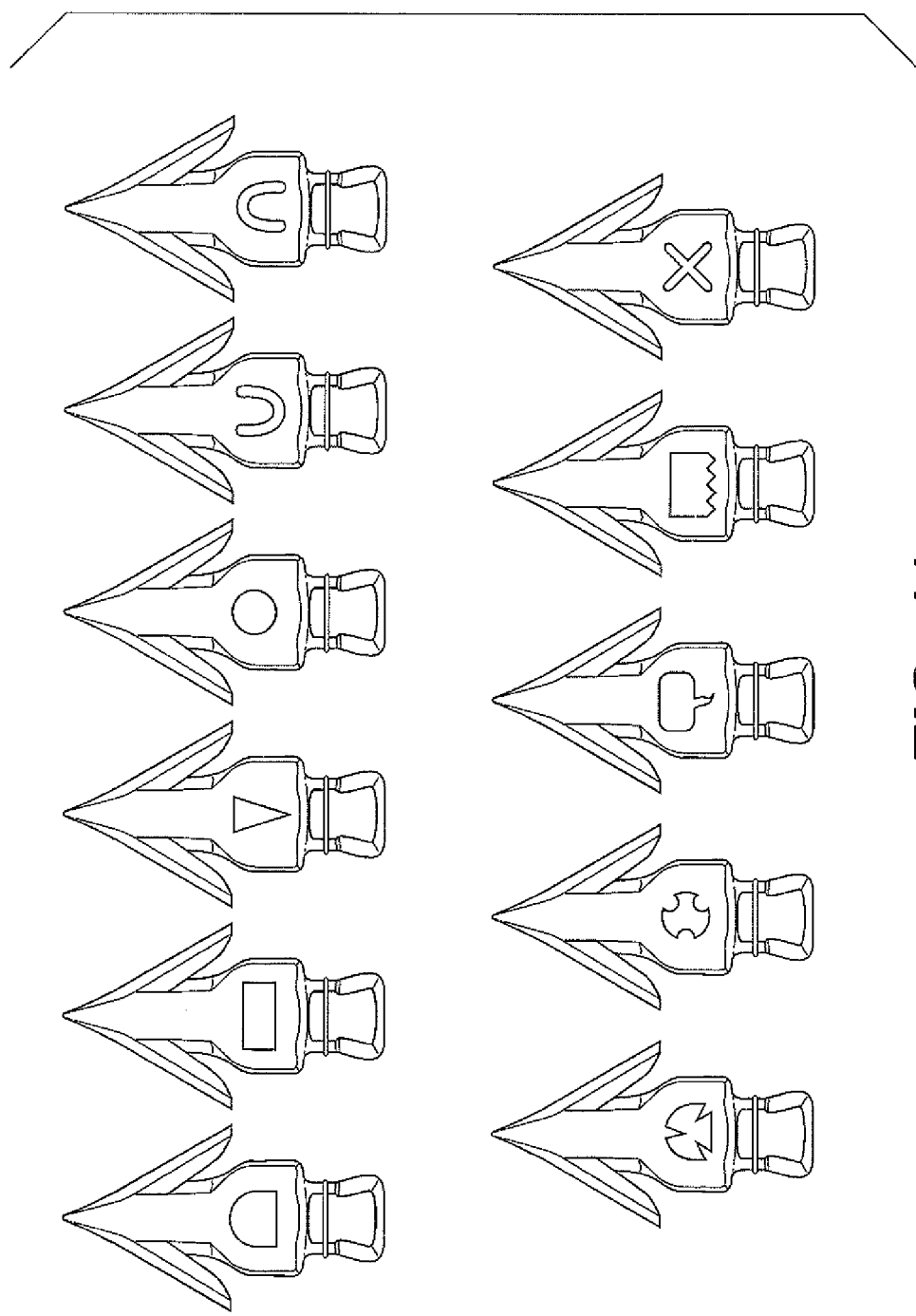
FIG. 11 illustrates cut-away views of exemplary tissue anchors.

According to one embodiment, at least one of the tissue anchors, such as tissue anchor 150, contains an aperture that is normal to the longitudinal axis of the anchor. This is illustrated in FIGS. 9A-9B and FIG. 11. FIG. 9A illustrates anchor 150a having barbs 151a, and aperture 152a configured to receive mesh arm 160. The aperture 151a and mesh arm 160 are respectively sized so that movement of arm 160 therethrough is restricted. The degree of restriction will depend on the fit between the arm and the edges of the aperture. According to one embodiment, the arm 160 and aperture 152a are relatively sized so that a slippage resistance in an amount of force ranging from 4 ounces to 6 pounds, for example 2 to 6 pounds, or 1 to 2 pounds, is required to pull 1 cm of the arm through the anchor aperture. FIG. 9B illustrates tissue anchor 150b having a triangularly-shaped aperture 152b. Arm 160 is received in aperture 152b, and exemplary feature 153b (the distal end of aperture 152b) assists in resisting movement of the arm. Additional exemplary tissue anchors are illustrated in FIG. 11.

Figure 12B:
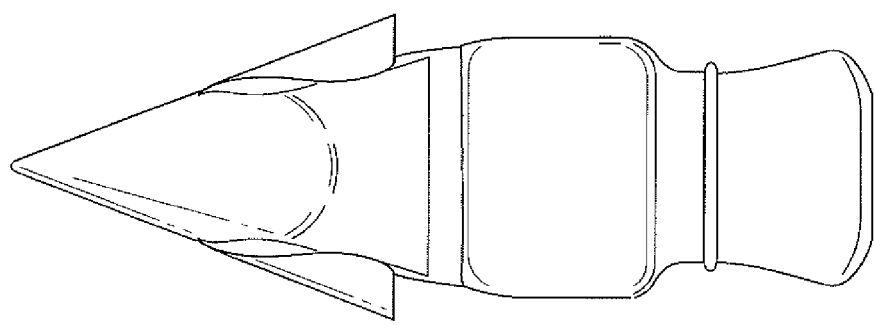
FIGS. 12A-12B illustrate bottom and side views of an exemplary tissue anchor.
Figure 12A:
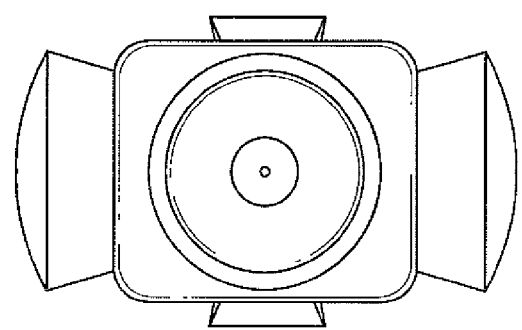

FIG. 12A illustrates a bottom view of an exemplary tissue anchor 150 according to the present disclosure. According to one embodiment, the tissue anchor has a longitudinal axis defined by a lumen. According to one embodiment, the lumen is configured to receive a pin that can pierce, and thereby anchor into position, arm 160. FIG. 12B illustrates a side view of tissue anchor 150.

Figure 10:
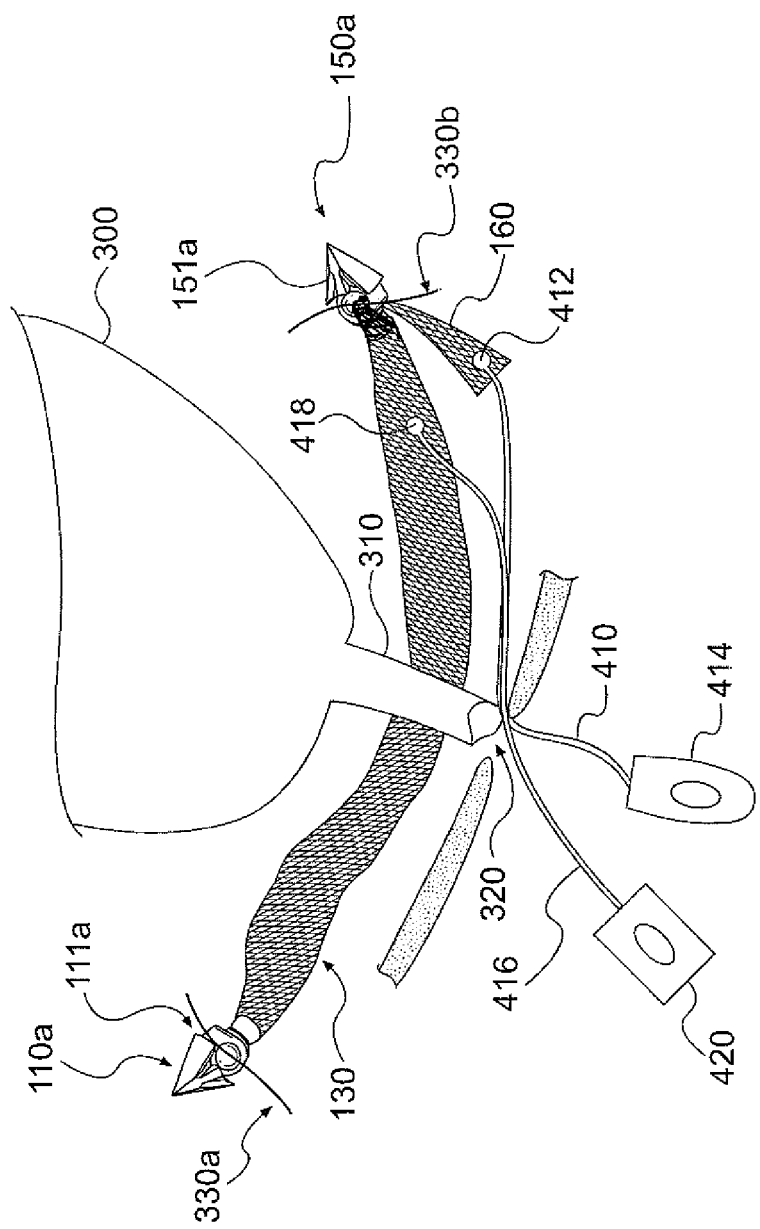
FIG. 10 illustrates an embodiment of a tissue support system.

FIG. 10 illustrates another embodiment in accordance with the present disclosure. A tissue support portion 130 is disposed underneath urethra 310 to assist in managing the flow of urine from bladder 300. Anchors 110a and 150a having barbs 111a and 151a, respectively, are anchored in the two obturator membranes 330a and 330b, respectively. A first adjustment suture 410 is attached to arm 160 at location 412. The distal end of first adjustment suture 410 is attached to tab 414. A second adjustment suture 416 is attached to tissue support portion 130 at location 418. The distal end of adjustment suture 416 is attached to tab 420. Both adjustment sutures 416 and 410 are configured to be disposed outside vaginal incision 320. According to various embodiments, and like the tissue anchors and the tissue support system, the adjustment sutures can be bioabsorbable.

Once the anchors 110a and 151a are securely anchored in the two obturator membranes, the surgeon may adjust the amount of tension exerted by tissue support portion 130 on urethra 310. According to one embodiment, the tension may be decreased by pulling suture 416 via tab 420. Alternatively, tension may be increased by pulling on suture 410 via tab 414. According to various embodiments, the adjustment sutures 410 and 416 may be differently colored to aid in identification. According to one embodiment, tabs 414 and 420 are differently shaped, differently colored, and/or marked to aid in distinguishing one suture from the other. According to another embodiment, sutures 410 and 416 are each in the form of a loop (not shown) that freely passes through respective points 412 and 418. That way, when the loops are cut following final tensioning of the implant, the entire length of suture is removed from the body.

According to various embodiments, immediately after the implant is tensioned, sutured 410 and 416 are cut and removed, and incision 320 is sutured closed. According to another embodiment, the implant is initially tensioned, and the incision is temporarily sutured and/or packed. The patient returns to the surgeon after 12 to 72 hours, and the patient's degree of continence or retention is reviewed. A final adjustment is made to the implant via tabs 414 and/or 420, the sutures 410 and 416 are cut and removed, and incision 320 is sutured closed.

The tissue anchors disclosed herein may be constructed from any biocompatible material, including stainless steel, polypropylene, and absorbable materials, including but not limited to polylactic acid, polyglactin, and polyglycolic acid, or other materials commonly used in absorbable surgical materials. According to various embodiments, the anchors disclosed herein can be of any dimension suitable to withstand particular pulling forces. The anchors can range in length from, for example, 5 mm to 20 mm, for example 10 mm to 15 mm, such as 10.1, 10.2, 10.3, 10.4, or 10.5 mm. The anchors have a thickness ranging from 1 mm to 5 mm, for example 2 mm to 3 mm thick. The anchors have a base of approximately 2.5 mm, for example 2.2 mm to 2.3 mm.

With reference to FIG. 1, the tissue support system 10 may further include stylet 185. Stylet 185 is configured for insertion into gripping feature 180, and then into the lumen 166 of arm 160. Stylet 185 includes a shaft 190 having a proximal end 194 and distal end 192, gripping feature 196, and a distal end 198. Stylet 185 can range in length from, for example, 12 cm to 25 cm, including 18 cm to 22 cm, such as 21 cm.

Figure 2:
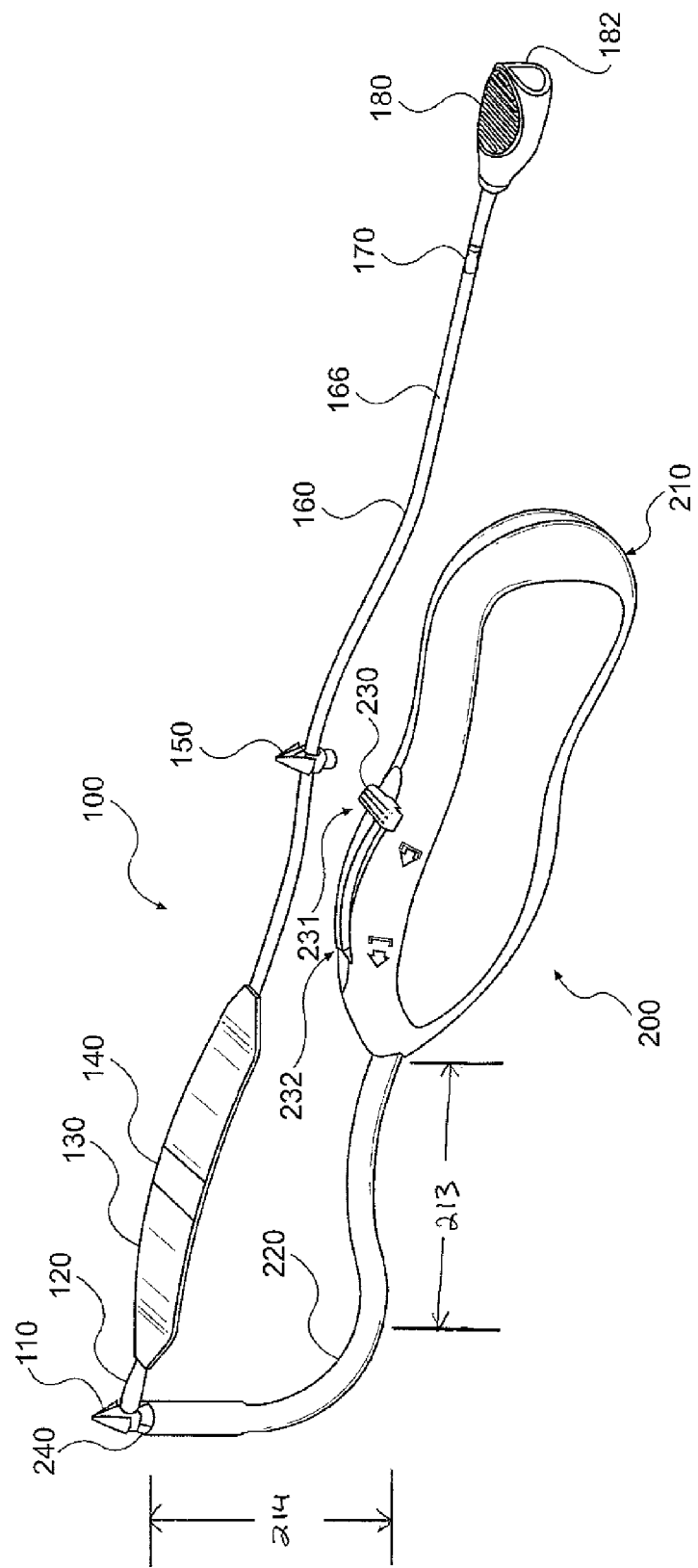
FIG. 2 illustrates an aspect of an implantable tissue support member and an introducer needle.
Figure 3:
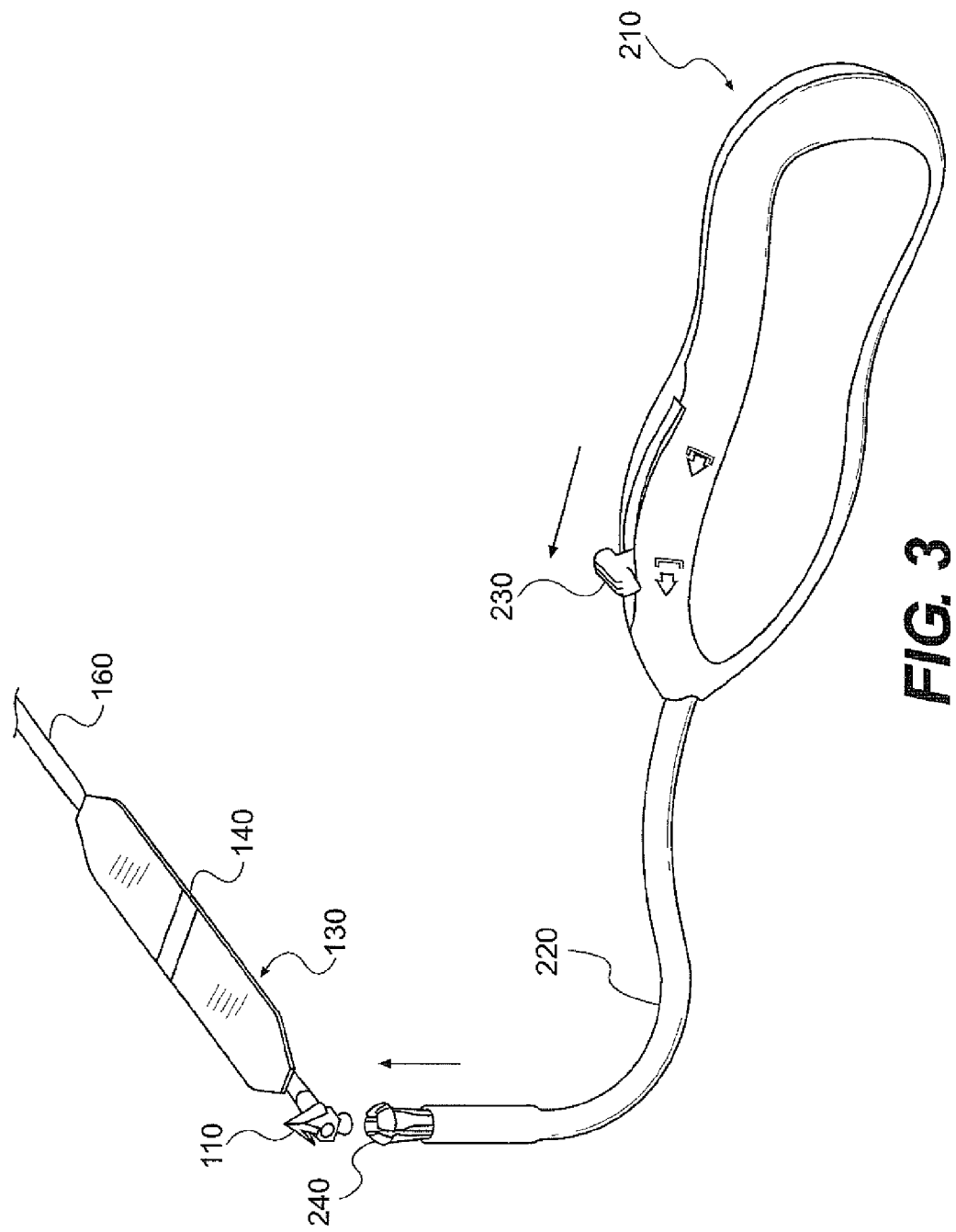
FIG. 3 illustrates a tissue anchor being released from an introducer needle.

The tissue support system may further comprise introducer needle 200 having a handle 210, shaft 220, collet 240 configured to releasably secure a tissue anchor, and manually operable actuator 230. The actuator 230 is configured to secure a tissue anchor to the collet 240 when in position 231 (FIG. 2), and release the tissue anchor when moved to position 232 (FIG. 3). The illustrated introducer needle 200 has a curved shaft 220, where the curve is in substantially the same plane as the handle. With reference to FIG. 2, shaft 220 can have a length 213 ranging from 3 cm to 7 cm, such as 4 cm to 6 cm, for example 5 cm. Shaft 220 can have a length 214 ranging from 3.5 cm to 5.5 cm, for example 4 cm to 5 cm, and 4.5 cm. According to various embodiments, shaft 220 is sized and shaped so that it snugly rotates around the ischiopubic ramus when an anchor is inserted in the region of the obturator foramen. According to another embodiment, the shaft has a helical shape. According to this embodiment, the system may be provided to a clinician with two helically-shaped needles, one for each side of a patient's anatomy.

FIGS. 1-6 illustrate locking member 170 disposed in lumen 166 in accordance with the present disclosure. According to various embodiments, the locking member 170 is constructed from polypropylene. The locking member 170 can have any size suitable for its intended purpose. By way of non-limiting example, the locking member has a diameter ranging from 1 mm to 2 mm, for example 1.2 mm to 1.8 mm, a width ranging from 1.5 mm to 2.5 mm, and a length ranging from 2.5 mm to 5.5 mm, for example 4.5 mm.

Figure 4:
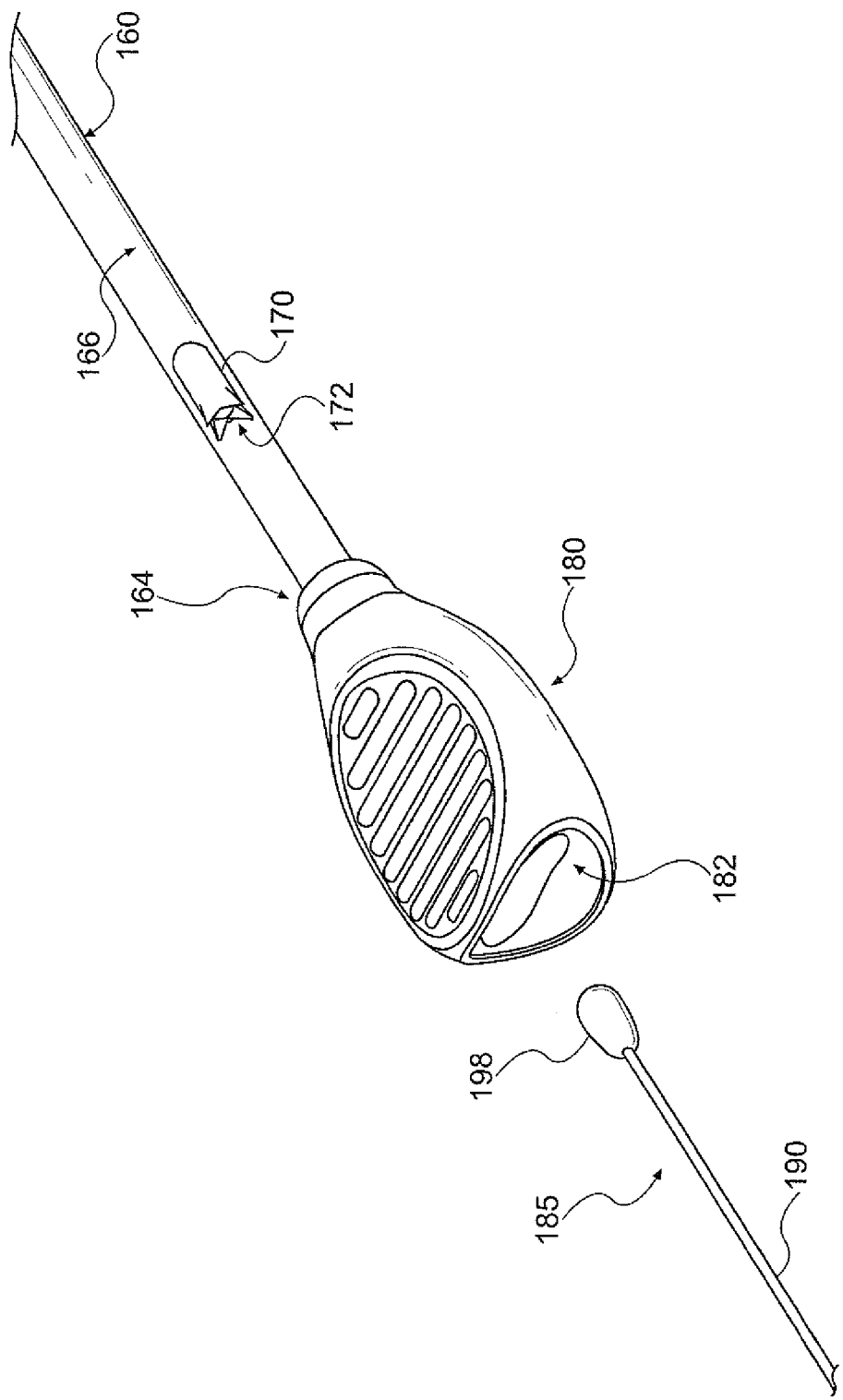
FIG. 4 illustrates a stylet being urged into a lumen.

With reference to FIG. 4, the locking member 170 is configured to be initially disposed within the lumen 166 of arm 160 at a location proximal to grasping feature 180. After anchor 150 is set in a desired tissue location, arm 160 is fixed in position relative to the locking feature until it abuts anchor 150. The sliding can be accomplished by insertion of flexible stylet 185 through lumen 182 in grasping feature 185, which lumen is in fluid communication with lumen 166 in arm 160. The distal end 198 of stylet 185 contacts locking member 170, and urges the locking member in the direction of anchor 150. Movement of the locking member in the reverse direction, i.e., towards end 164 of arm 160, is arrested by the prongs 172. When the anchor stop is urged towards the end 164, the prongs 170 will tend to anchor into the mesh, thus arresting further movement.

Figure 5:
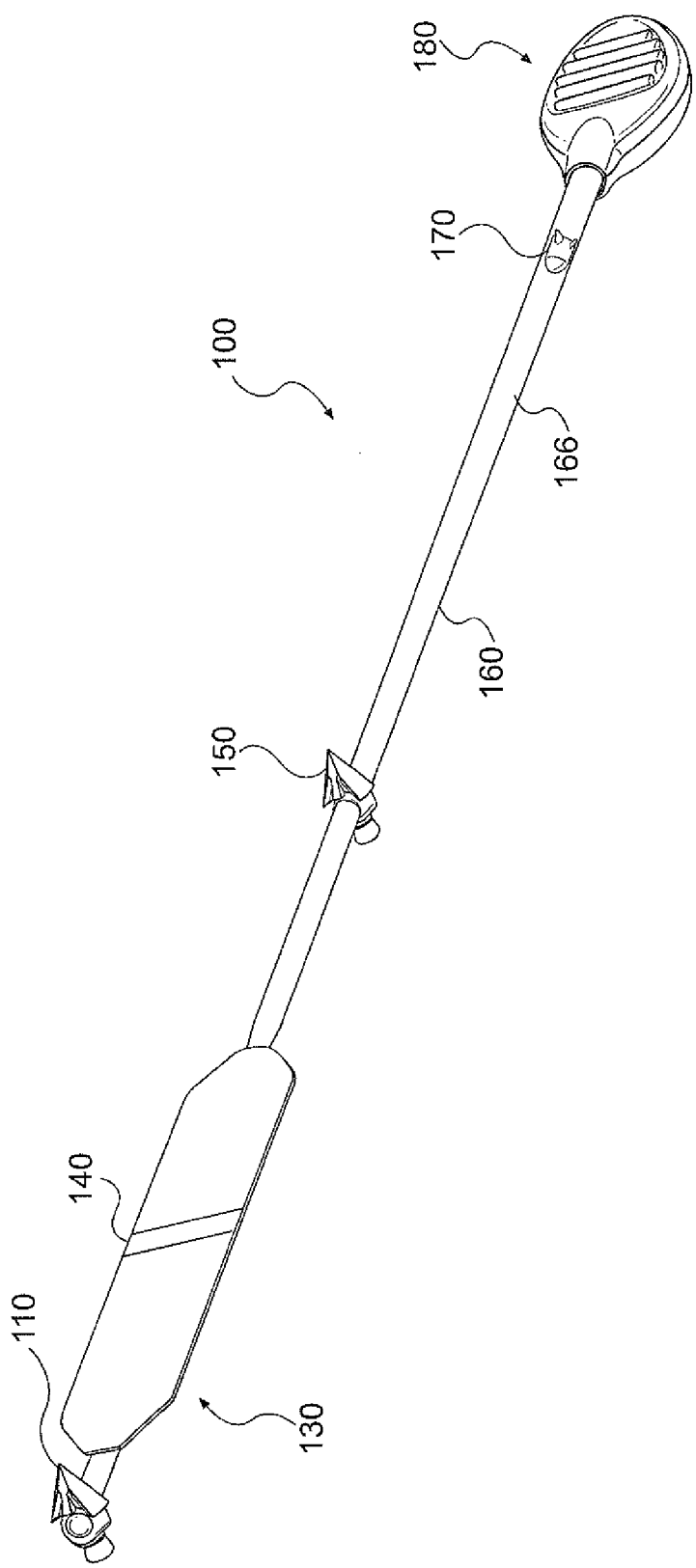
FIG. 5 illustrates a view of a tissue support member.
Figure 6:
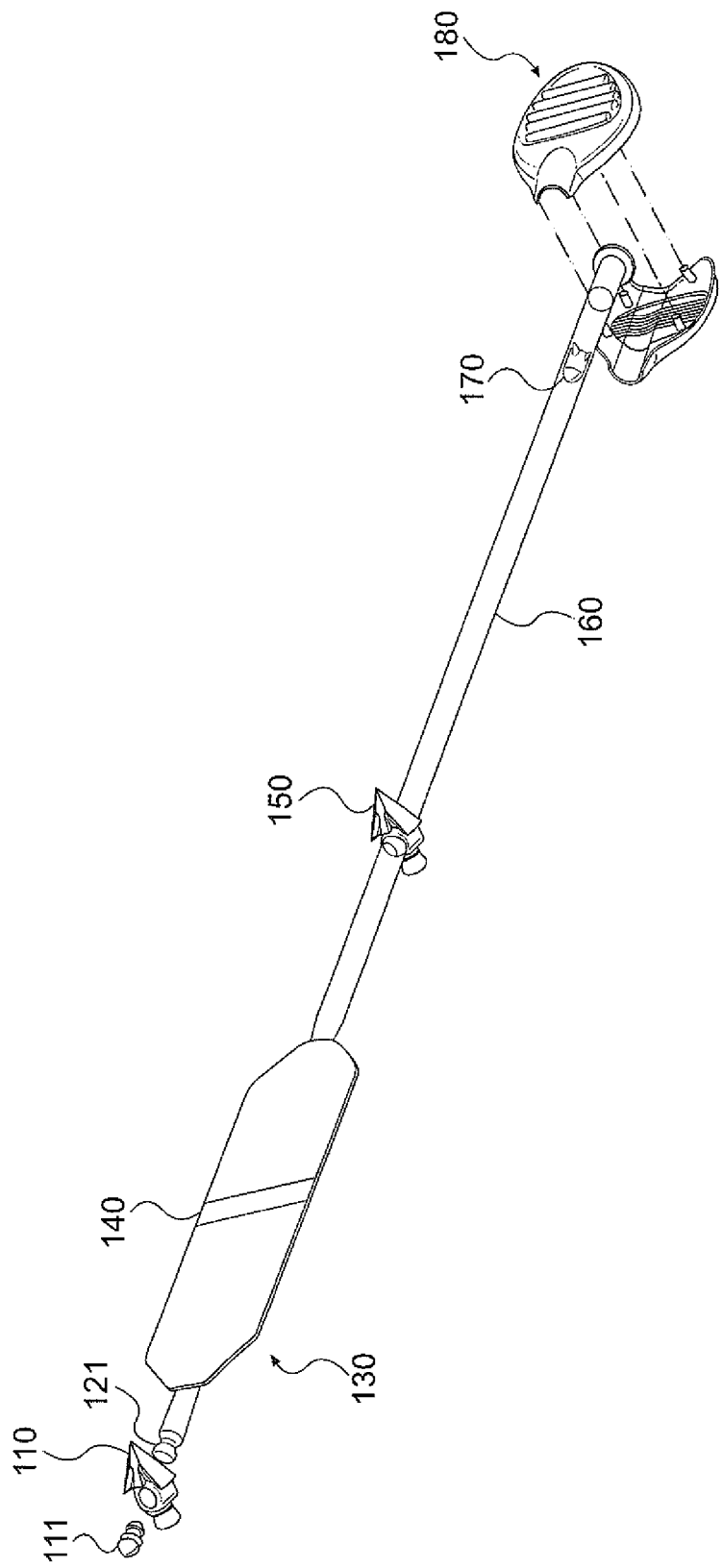
FIG. 6 illustrates an exploded view of a tissue support member.
Figure 7:
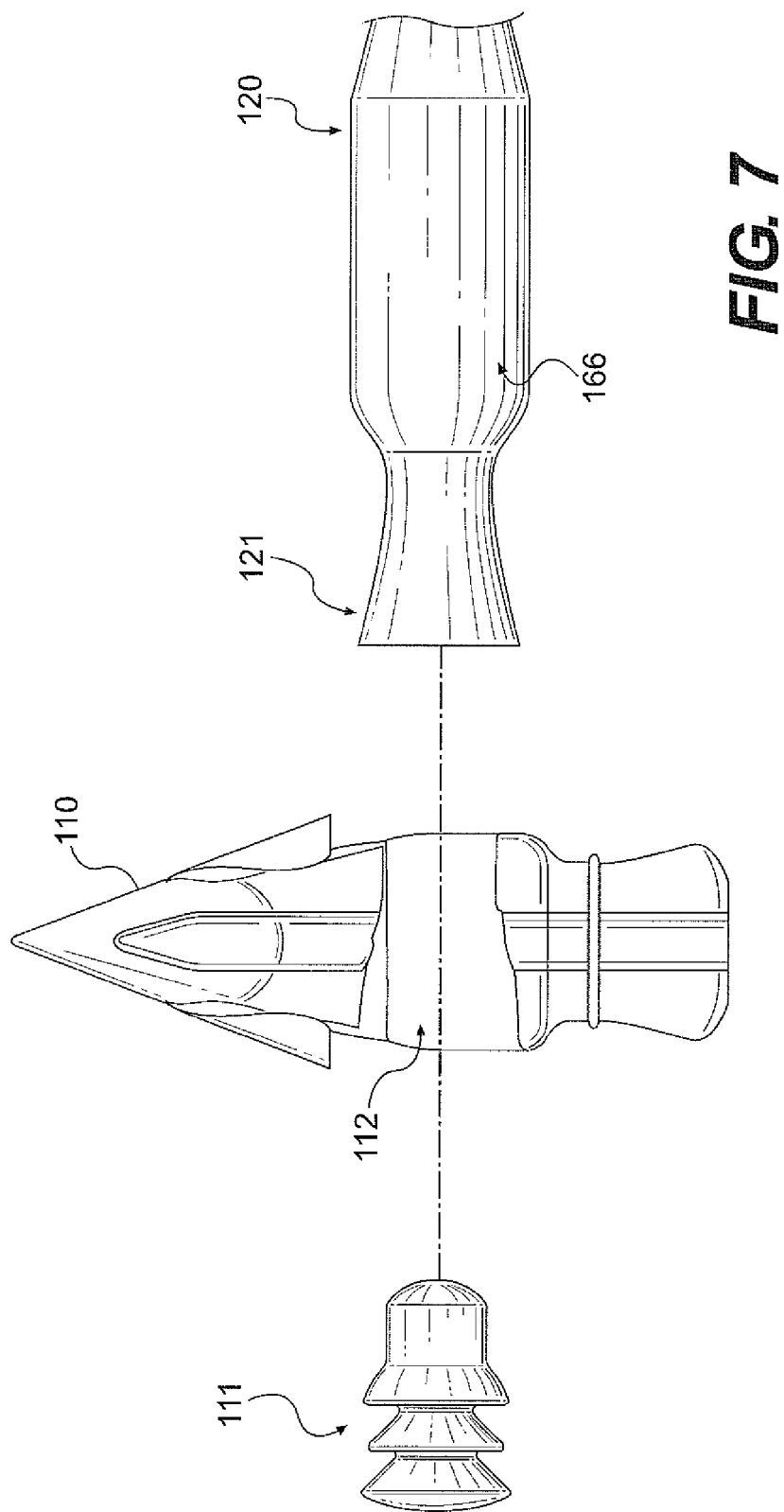
FIG. 7 illustrates a view of one aspect of a tissue support member.
Figure 8:
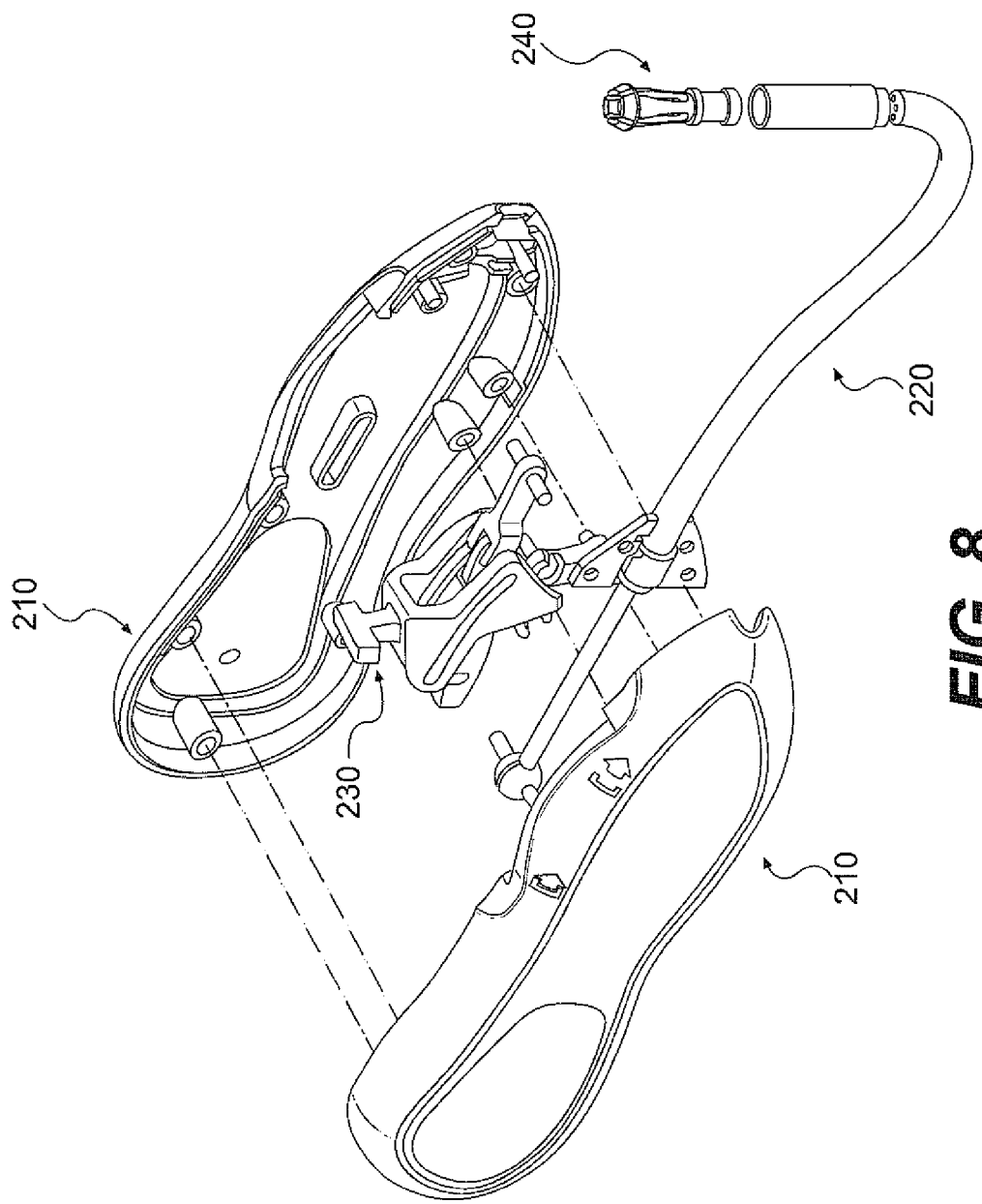
FIG. 8 illustrates an exploded view of an introducer needle.

FIG. 5 illustrates another view of the implantable tissue support member 100. FIG. 6 illustrates a partially exploded view of the tissue support member. FIG. 7 illustrates one embodiment of the fixation of anchor 110 to arm 120. End 121 of arm 120 is inserted into aperture 112 of anchor 110. Plug 111 is then inserted into lumen 166 and aperture 112, thereby providing a friction fit between the plug 112, the arm 120, and anchor 110.

The tissue support system in accordance with the present disclosure can be used to restore correct support to various types of tissue. For example, the system can be used to treat female and male urinary incontinence, for example stress incontinence. The system can be used to treat fecal incontinence. In addition, the system can be used for pelvic floor repair, such as pelvic organ prolapse, by fixing a tissue support portion to ligament and/or muscle for anterior, posterior, and apical vaginal vault repair.

According to one embodiment, the tissue support system disclosed herein comprises a urethral sling. According to one embodiment, a procedure for implanting the urethral sling generally comprises making a mid-urethral incision and dissecting the vaginal tissue out laterally in the direction of the superior-medial aspect of the obturator foramen. The ends of the sling are then passed through the obturator internus muscle/obturator membrane using an introducer device. According to one embodiment, two exit incisions are made in the groin to allow for exteriorization of the introducer needle and sling ends. These exit incisions allow for adjustment of the sling tension under the urethra using the free arms of the mesh at the exit incisions. According to another embodiment of the present disclosure, the urethral sling does not require any exit incisions because mesh adjustment can be done at the vaginal incision.

The following illustrates one way in which a tissue support system in accordance with the present disclosure may be used to treat female urinary incontinence. The patient is placed in a dorsal lithotomy position with hips in flexion at approximately 90 degrees and the buttocks even with the edge of the table. Standard operative preparation of the surgical site is completed, and the bladder is emptied with a Foley catheter. The mid-urethra is identified by first locating the external urethral meatus and then the bladder neck by identifying the Foley catheter bulb.

Hydro-dissection is performed by injecting a solution (e.g., 1% lidocaine with epinephrine) at the midline between the vaginal wall and urethra, thereby creating a urethro-vaginal space. Additional hydro-dissection can be performed by injecting solution laterally towards the cephalad aspect of the ischiopubic ramus in order to better identify the lateral sulci. Allis clamps are placed at the level of the mid-urethra on the anterior vaginal wall.

A small (approximately 1.5 cm) incision is made in the anterior vaginal wall beginning approximately 1 cm under the urethral meatus. The depth of the incision may extend into the vaginal muscularis. The urethra is gently freed from the anterior vaginal wall. Next, dissection is made using scissors (e.g., Metzenbaum scissors) laterally in a 45 degree angle until the tip of the scissors makes contact with the medial-cephalad aspect of the ischiopubic ramus (approximately 1-2 cm). This procedure is then repeated on the contralateral side.

The introducer needle 200 is loaded with anchor 110, as shown in FIG. 2. The introducer is then inserted into the vaginal dissection laterally through one of the dissected planes toward the cephalad aspect of the ischiopubic ramus. The introducer 200 is angled towards the superior-medial aspect of the obturator foramen. Once the fixed anchor is behind the ischiopubic ramus, anchor 110 is pushed into the tissue until it is slightly beyond the ramus.

The handle 210 is pivoted to insert the anchor 110 through the obturator internus muscle/membrane at the superior-medial aspect of the obturator foramen, such that the orienting indicia 140 is at or slightly past the midurethra (about 0.5 cm) in the direction of insertion. A distinctive pop may be heard, indicating perforation of the muscle/membrane. The anchor 110 is released by pushing the actuator 230 forward from position 231 to position 232 in the introducer handle 210. The introducer is then gently retracted by reversing through the insertion path.

After anchor 110 is released from collet 240, gentle traction is applied to the sub-urethral sling to confirm secure fixation in the tissue.

Next, adjustable anchor 150 is loaded into the introducer and secured by retracting the manual actuator 230 on the handle 210 from position 232 to position 231. A slight "click" may be felt or heard, confirming secure loading. At this point in the procedure, care is taken to ensure the implant is not twisted.

Next, it may be desirable to confirm at least 4 cm of adjustable mesh between the tissue support portion 130 and the anchor 150 prior to insertion.

The anchor 150 is inserted in the contralateral dissection plane, and the introducer needle 200 is oriented towards the superior-medial aspect of the obturator foramen. Anchor 150 is pushed into the tissue slightly beyond the ischiopubic ramus, and handle 210 is pivoted to insert anchor 150 through the obturator internus muscle/membrane in the superior-medial aspect of the obturator foramen.

Anchor 150 is released from collet 240 by pushing the actuator 230 from position 231 to position 232 in the introducer handle 210. Introducer needle 200 is retracted by reversing through the insertion path. After anchor 150 is released, gentle traction is applied on the tissue support system 100 to confirm secure fixation in the tissue.

Grasping feature 180 is gently pulled to adjust the tension exerted by the tissue support portion 130 on the urethra. To aid in adjustment, a finger is inserted vaginally to stabilize anchor 150 at the obturator internus muscle. The sling can also be loosened by using gentle counter-traction on the tissue support portion 130 on the side closest to anchor 150. A thin, blunt instrument (such as a hemostat) between the urethra and the sub-urethral sling may be used as a spacer to aid in setting the appropriate tension. A cough or créde test can also be employed to achieve the appropriate tension. The orienting indicia 140 should be visible at the midline, no more than 1 cm away from the urethra in either direction.

Once proper tensioning is achieved, stylet 185 is inserted into lumen 182 of gripping feature 180. The stylet 185 is inserted into lumen 166 to urge locking member 170 into place at anchor 150. When properly seated, the stylet 185 will bow, signifying that the locking member 170 is in the proper location and the tissue support member has been secured. Once anchor 150 is locked into position, additional tightening can be achieved using the gripping feature 180.

Stylet 185 is removed after final securement of the tissue support member 100. According to one embodiment, arm 160 is cut between anchor 150 and end 164. The vaginal incision is then closed using suture. According to various embodiments, the incision is temporarily closed and packed around arm 160. This would allow the clinician to post-operatively modify the amount tension exerted by the implant on the urethra. Once desired degree of tension is obtained and confirmed, the anchor 150 can optionally be fixed to arm 160, and the remaining material can be cut and, in the case wherein the implant is constructed of non-bioabsorbable material, be removed from the body.

According to various embodiments, a sheath can enclose at least a portion of the tissue support member disclosed herein to facilitate their passage into tissue. In such an embodiment, the tissue support member, or at least the support portion thereof, is sandwiched between two sheaths. The sheath sides are suitably made out of a material with a low coefficient of friction, such as polytetrafluoroethylene (PTFE). According to another embodiment, the tissue support member is implanted without a sheath.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise. All publications, patent applications, patents, and other references mentioned herein are expressly incorporated by reference in their entirety.

Also, unless otherwise indicated, all numbers expressing quantities of physical parameters and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Numerical ranges given throughout this specification will include every narrower numerical range that falls within such broader numerical range, as if such narrower numerical ranges were all expressly written herein.

What is claimed is:

1. A tissue support system including an implantable tissue support member comprising:
    a tissue support portion;
    a first arm having a first end joined to a first end of the tissue support portion;
    a second arm having a first end joined to a second end of the tissue support portion, the second arm defining a lumen, the second arm being formed from a tubular knit construction of a mesh material;
    a first tissue anchor fixed to a second end of the first arm;
    a second tissue anchor slidably positioned over the second arm; and
    a locking member disposed in the lumen of the second arm between the second tissue anchor and a second end of the second arm.

2. The tissue support system according to claim 1, wherein the second tissue anchor includes a head with a tissue penetrating tip and a base.

3. The tissue support system according to claim 2, wherein the base includes an aperture through which the second arm is positioned.

4. The tissue support system according to claim 3, wherein the aperture is normal to a longitudinal axis of the second tissue anchor.

5. The tissue support system according to claim 3, wherein the aperture resists unconstrained movement of the second arm therethrough.

6. The tissue support system according to claim 1, wherein the locking member is shaped to permit movement toward the second tissue anchor, but to resist movement away from the second tissue anchor.

7. The tissue support system according to claim 1, further comprising a stylet for introduction into the lumen of the second arm, and for urging the locking member in the direction of the second tissue anchor.

8. The tissue support system according to claim 1, further comprising an introducer needle capable of releasably securing the first and second tissue anchors.

9. The tissue support system according to claim 8, wherein the introducer needle comprises a shaft and a handle.

10. The tissue support system according to claim 9, wherein the shaft has a curved portion.

11. The tissue support system according to claim 10, wherein the shaft has a substantially helical shape.

12. The tissue support system according to claim 9, wherein the introducer needle comprises a collet at the distal end of the shaft.

13. The tissue support system according to claim 9, wherein the handle comprises a manually operable mechanism for releasing the first and second tissue anchors from the distal end of the shaft.

14. The tissue support system according to claim 1, wherein the tissue support portion comprises orientating indicia.

15. The tissue support system according to claim 14, wherein the orientating indicia comprises a colored feature in the center of the tissue support portion.

16. The tissue support system according to claim 1, wherein the first and second tissue anchors are shaped to penetrate tissue when urged in a first direction, and resist movement in a second direction opposite of the first direction.

17. The tissue support system according to claim 1, wherein the tissue support portion, the first arm, and the second arm are formed from mesh.

18. The tissue support system according to claim 17, wherein the tissue support portion is formed from a single layer of mesh.

19. The tissue support system according to claim 17, wherein the tissue support portion, the first arm, and the second arm are constructed from a unitary tubular member.

20. A tissue support system including an implantable tissue support member comprising:
   a tissue support portion;
   a first arm having a first end joined to a first end of the tissue support portion;
   a second arm having a first end joined to a second end of the tissue support portion, the second arm defining a lumen;
   the tissue support portion, the first arm, and the second arm constructed from a unitary tubular mesh member;
   a first tissue anchor fixed to a second end of the first arm;
   a second tissue anchor slidably positioned over the second arm; and
   a locking member disposed in the lumen of the second arm between the second tissue anchor and a second end of the second arm.

* * * * *